US010874062B2

(12) United States Patent
Fujiyama et al.

(10) Patent No.: US 10,874,062 B2
(45) Date of Patent: Dec. 29, 2020

(54) MOISTURE CONTENT OBSERVATION DEVICE, MOISTURE CONTENT OBSERVATION METHOD, AND CULTIVATION DEVICE

(71) Applicant: PANASONIC INTELLECTUAL PROPERTY MANAGEMENT CO., LTD., Osaka (JP)

(72) Inventors: Takeshi Fujiyama, Fukuoka (JP); Yuuji Terashima, Fukuoka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 364 days.

(21) Appl. No.: 16/066,216

(22) PCT Filed: Feb. 17, 2017

(86) PCT No.: PCT/JP2017/005863
§ 371 (c)(1),
(2) Date: Jun. 26, 2018

(87) PCT Pub. No.: WO2017/150213
PCT Pub. Date: Sep. 8, 2017

(65) Prior Publication Data
US 2020/0236877 A1    Jul. 30, 2020

(30) Foreign Application Priority Data

Feb. 29, 2016  (JP) ................................ 2016-038226

(51) Int. Cl.
*G01N 21/3554* (2014.01)
*G01N 21/359* (2014.01)
(Continued)

(52) U.S. Cl.
CPC ......... *A01G 27/003* (2013.01); *G01N 21/359* (2013.01); *G01N 21/3554* (2013.01);
(Continued)

(58) Field of Classification Search
CPC ................................................. G01N 21/3554
See application file for complete search history.

(56) References Cited

U.S. PATENT DOCUMENTS 5,130,545 A * 7/1992 Lussier .................... A01G 7/00
                                                          250/458.1
5,179,422 A * 1/1993 Peterson .................. G01N 21/94
                                                          250/559.41
(Continued)

FOREIGN PATENT DOCUMENTS

EP           2405258 A2      1/2012
EP           3312590 A1 *   4/2018  ......... G01N 21/3581
JP        2001-272373      10/2001

OTHER PUBLICATIONS

The Extended European Search Report dated Nov. 27, 2018 for European Patent Application No. 17759682.2.
(Continued)

*Primary Examiner* — Shawn Decenzo
(74) *Attorney, Agent, or Firm* — Greenblum & Bernstein, P.L.C.

(57) ABSTRACT

First beam source radiates a near infrared reference beam of 905 nm, in which light tends not to be absorbed in water toward a leaf of a plant. Second beam source radiates a near infrared measuring beam of 1550 nm, in which light tends to be absorbed in water toward the leaf of the plant. Threshold level setter/water content index detector calculates a water content index of one leaf as a total sum Σ Ln($I_{905}/I_{1550}$) of the reflection intensity ratio. Controller displays a graph representing a total sum of water content of the leaf and a pixel average value as a time-transition of the water content contained in the plant from the start of the measurement period on a UI screen of a monitor. Viewed from the first and second beam sources, a white reference substrate covering a back surface of the leaf is disposed on the leaf of the plant.

8 Claims, 20 Drawing Sheets

(51) Int. Cl.
*G01N 21/84* (2006.01)
*A01G 27/00* (2006.01)
*G01N 33/00* (2006.01)

(52) U.S. Cl.
CPC ......... *G01N 21/84* (2013.01); *G01N 33/0098* (2013.01); *G01N 2021/8466* (2013.01); *G01N 2201/06113* (2013.01)

(56) References Cited

U.S. PATENT DOCUMENTS

| | | | | |
|---|---|---|---|---|
| 5,436,456 A | * | 7/1995 | Tucker | G01N 21/3554 250/339.1 |
| 6,115,644 A | * | 9/2000 | Petty | G01N 21/3554 198/418.1 |
| 9,128,049 B2 | * | 9/2015 | Groz | G01N 21/3151 |
| 10,126,234 B2 | * | 11/2018 | Fujiyama | G01N 21/3151 |
| 10,309,896 B2 | * | 6/2019 | Fujiyama | G01N 21/3554 |
| 10,613,024 B2 | * | 4/2020 | Fujiyama | G01N 21/359 |
| 2016/0302351 A1 | * | 10/2016 | Schildroth | B64C 39/024 |
| 2017/0115210 A1 | * | 4/2017 | Fujiyama | G01N 21/84 |
| 2018/0372624 A1 | * | 12/2018 | Fujiyama | G01N 33/0098 |
| 2019/0137385 A1 | * | 5/2019 | Nappez | G01N 21/359 |
| 2019/0265162 A1 | * | 8/2019 | Fujiyama | G06T 7/001 |
| 2019/0271000 A1 | * | 9/2019 | de Godoy Lusso | C12N 15/8218 |
| 2020/0200683 A1 | * | 6/2020 | Aronov | A01G 25/16 |

OTHER PUBLICATIONS

Gaulton R et al: "The potential of dual-wavelength laser scanning for estimating vegetation moisture content", Remote Sensing of Environment, Elsevier, XX, vol. 132, Jan. 31, 2013 (Jan. 31, 2013), pp. 32-39, XP028522997.

Official Communication issued in International Pat. Appl. No. PCT/JP2017/005863, dated Apr. 11, 2017.

* cited by examiner

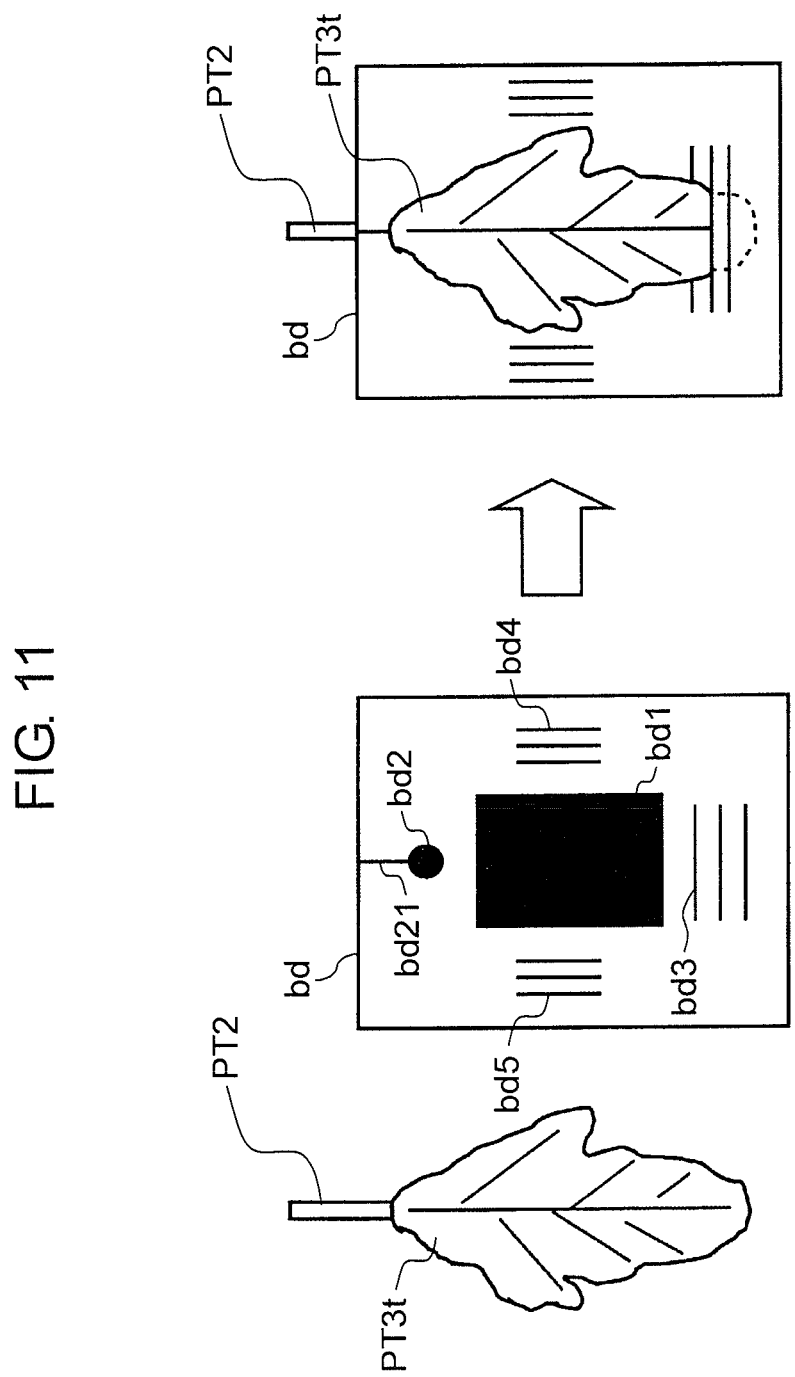

MOISTURE CONTENT OBSERVATION DEVICE, MOISTURE CONTENT OBSERVATION METHOD, AND CULTIVATION DEVICE

TECHNICAL FIELD

The present disclosure relates to a device for observing water content which observes water content contained in a plant, a method for observing water content, and a cultivation device.

BACKGROUND ART

There is a potential difference inside and outside of a cell in a normal plant and electromotive force is generated. It is possible to describe a mechanism which generates such electromotive force based on, for example, an electrophysiological model of an axial organ of a higher plant. In particular, various methods are suggested in which a state of a root of the plant (for example, water stress) is examined non-destructively utilizing electromotive force between the root and soil.

As a prior technique in which water stress in a plant is measured utilizing the method described above, for example, Patent Document 1 discloses connecting a first nonpolarizable electrode to the plant, connecting a second nonpolarizable electrode to soil in which the plant is planted, and providing a potentiometer between the two nonpolarizable electrodes. It is possible to measure water stress which is received by the plant by measuring electromotive force between both nonpolarizable electrodes using the potentiometer.

An object of the present disclosure is to suggest quantitatively and time-serially transition of a water content contained in a plant without independently determining based on experiences, intuitions or the like by visually observing a leaf of a plant that is a cultivation target a farmer, and teach early a state of the application of water stress to the plant and whether or not the plant is partially necrosed.

CITATION LIST

Patent Literature

PTL 1: Japanese Patent Unexamined Publication No. 2001-272373

SUMMARY OF THE INVENTION

A device for observing water content in a plant of the present disclosure includes a first light source which radiates a near infrared laser reference beam of a first wavelength having a characteristic in which light tends not to be absorbed in water while sequentially scanning toward the plant; a second light source which radiates a near infrared laser measuring beam of a second wavelength having a characteristic in which light tends to be absorbed in water while sequentially scanning toward the plant; an output unit that outputs an invisible light image of a target portion to be observed of the plant; a water content calculation unit that repeatedly calculates the water content contained in each pixel area constituting the invisible light image based on reflection light of the near infrared laser reference beam and reflection light of the near infrared laser measuring beam, in a certain measurement period; and a controller that displays, as a time-transition of the water content in the target portion from start of the measurement period, a pixel average value of the water content in the target portion and a total sum of the water content in the target portion using the water content contained in the pixel area calculated by the water content calculation unit on a display unit in a comparative manner.

In addition, a cultivation device of the present disclosure is provided to the device for observing water content and a cultivation controller that performs irrigation with an initial irrigation amount set at start of the measurement period to the plant.

In addition, a method for observing water content in a device for observing water content in a plant of the present disclosure, the method includes radiating a near infrared laser reference beam of a first wavelength having a characteristic in which light tends not to be absorbed in water while sequentially scanning toward the plant, by a first light source; radiating a near infrared laser measuring beam of a second wavelength having a characteristic in which light tends to be absorbed in water while sequentially scanning toward the plant, a second light source; outputting an invisible light image of a target portion to be observed of the plant; repeatedly calculating the water content contained in each pixel area constituting the invisible light image based on reflection light of the near infrared laser reference beam and reflection light of the near infrared laser measuring beam, in a certain measurement period; and displaying, as a time-transition of the water content in the target portion from start of the measurement period, a pixel average value of the water content in the target portion and a total sum of the water content in the target portion using the water content contained in the pixel area calculated by the water content calculation unit on a display unit in a comparative manner.

According to the present disclosure, it is possible to suggest quantitatively and time-serially transition of a water content contained in a plant without independently determining based on experiences, intuitions or the like by visually observing a leaf of a plant that is a cultivation target a farmer, and teach early a state of the application of water stress to the plant and whether or not the plant is partially necrosed.

BRIEF DESCRIPTION OF DRAWINGS

FIG. 11 is a diagram which describes an example of attachment of the leaf on a white reference substrate.

DESCRIPTION OF EMBODIMENTS

Hereinafter, embodiments (hereinafter, referred to as present embodiment) in which a device for observing water content, a cultivation device, and a method for observing water content according to the present disclosure are specifically described are described in detail with reference to the drawings as appropriate. However, detailed description may be omitted as necessary. For example, detailed description of already well-known matter and overlapping description with respect to substantially the same configuration may be omitted. This is because the following description is prevented from unnecessarily becoming redundant, and a process of the inventor is easily set. Note that, drawings and the following description are provided by the inventor for sufficient understanding of the present disclosure, and thereby, the present disclosure is not intended to be limited to a subject described in the range of the claims.

Figure 1:
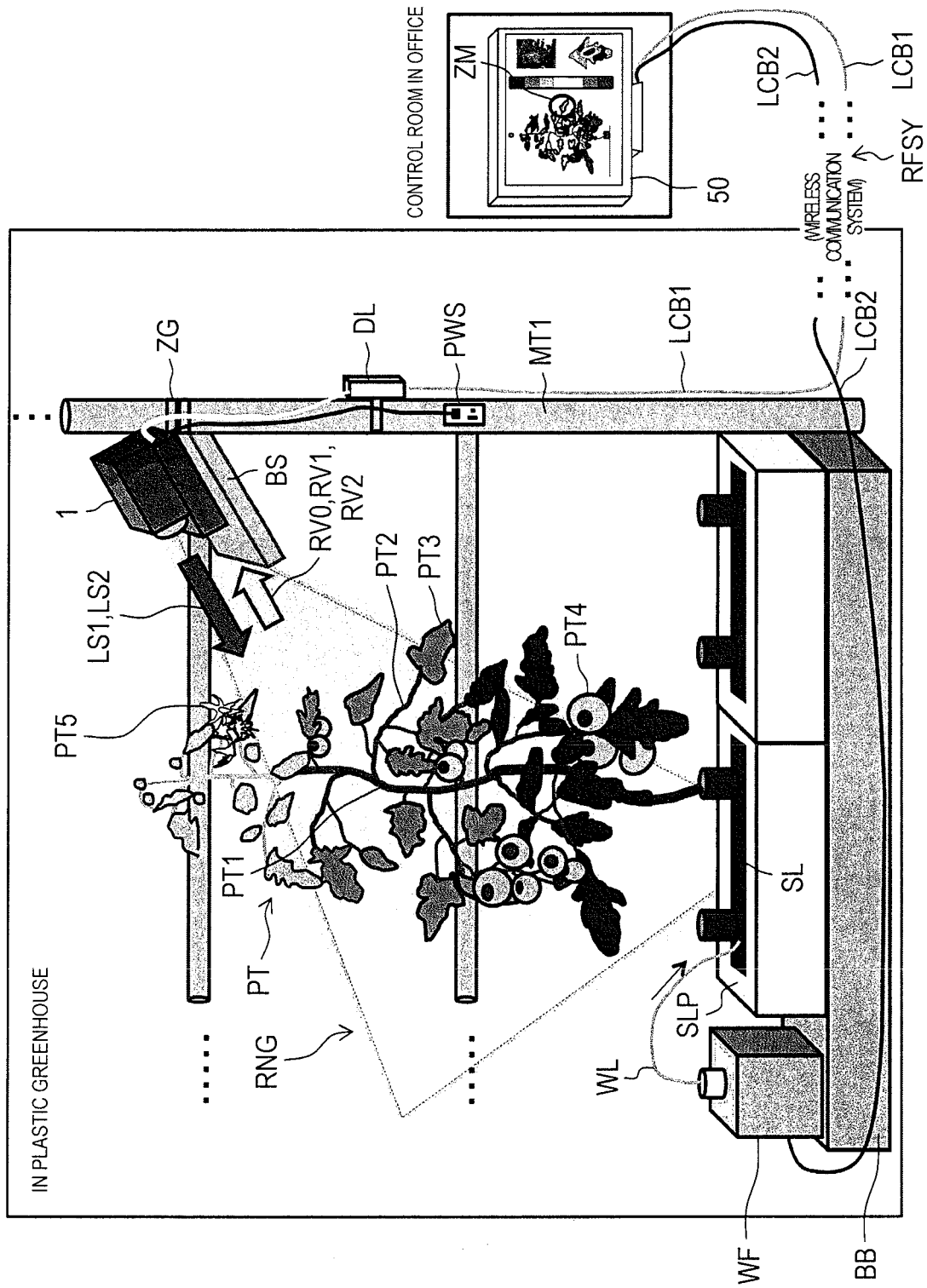
FIG. 1 is a conceptual explanatory diagram illustrating an example of usage circumstances of a plant detection camera in a first embodiment.

As an example of the device for observing water content of the present embodiment, description will be given by exemplifying plant detection camera 1 as illustrated in FIG. 1. In addition, the cultivation device of the present embodiment has a configuration of including plant detection camera 1 as illustrated in FIG. 1, fertilizer or water supply device WF as an example of a cultivation controller that supplies a fertilizer (for example, a liquid fertilizer) or irrigates the plant with a predetermined amount of the water content, and monitor 50 that displays (user Interface) screen 60 (refer to FIG. 14 and FIG. 15) or the like. Further, the present disclosure can realize a method for observing water content for executing each process performed by plant detection camera 1. Plant detection camera 1 of the present embodiment is able to detect a distribution state of presence or absence of water content in a target portion (for example, a leaf) of the plant. Hereinafter, the leaf is exemplified as a target portion of the plant, but the target portion of the plant is not limited to the leaf, and other parts such as a fruit, a stem, a flower, and a root may be used.

Here, an observation target of plant detection camera 1 of the present embodiment is the leaf or the part of the plant, and description is made by exemplifying a fruit vegetable that is given as a more specific example. Since sugar content of a fruit of a tomato is increased in growth of fruit vegetables such as, for example, the tomato, it is known that it is necessary for water or fertilizer to be in an insufficient state to some extent and not a state in which water or fertilizer is sufficiently supplied as a result of water or fertilizer of a root or a leaf being digested by a suitable amount in photosynthesis. For example, if sufficient water is supplied to the leaf, the leaf has a flat shape in a sound state. Meanwhile, when water of the leaf is equivalently insufficient, the shape of the leaf is bent. Meanwhile, when fertilizer in the soil is equivalently insufficient, a condition is generated of the leaf turning yellow and the like.

In the present embodiment below, an example is described in which plant detection camera 1 radiates laser beams of a plurality of types which are different in wavelength on the leaf of the plant, and detects water content of the leaf based on an intensity ratio of respective diffuse reflection light that are reflected on irradiation positions (in other words, an area indicating individual pixels constituting a captured image of the leaf irradiated with the laser beam) of the leaf.

(Outline of Plant Detection Camera)

FIG. 1 is a conceptual explanatory diagram illustrating an example of usage circumstances of plant detection camera 1 in a first embodiment. Plant detection camera 1 is installed at a fixed point within a greenhouse in which, for example, fruit vegetables such as the tomato are planted. In detail, for example, plant detection camera 1 is installed on base BS that is fixed to mounting jig ZG which is attached so as to interpose support column MT1 with a cylindrical shape extend in a vertical direction from the ground. Plant detection camera 1 operates by power to be supplied from power source switch PWS that is attached to support column MT1, and radiates reference beam LS1 and measuring beam LS2 that are a plurality of types of laser beams which have different wavelengths toward plant PT that is the observation target across irradiation range RNG.

Plant PT is, for example, a fruit vegetable plant such as the tomato, a root of plant PT which grows from soil SL that is filled in soil pot SLP which is installed on base BB, and plant PT has each of stem PT1, stalk PT2, leaf PT3, fruit PT4, and flower PT5. Fertilizer or water supply device WF is installed on base BB. Fertilizer or water supply device WF supplies the amount of water to be irrigated to soil spot SLP via, for example, cable WL according to an instruction from wireless communication system RFSY that is connected via local area network (LAN) cable LCB2. Thereby, since water is supplied to soil SL, the root of plant PT absorbs water, and transmits water to each part within plant PT (that is, stem PT1, stalk PT2, leaf PT3, fruit PT4, and flower PT5).

In addition, plant detection camera 1 receives diffuse reflection light RV1 and RV2 that are reflected on an irradiation position of plant PT which is radiated by reference beam LS1 and measuring beam LS2, and furthermore, receives ambient light RV0. As will be described later, plant detection camera 1 has an original camera function, and is able to image an image (that is, visible light image of plant PT within the greenhouse indicated in FIG. 1) within a default angle of view due to ambient light RV0 entering. Plant detection camera 1 outputs output data which includes various detection results (refer to description below) or image data to data logger DL based on diffuse reflection light RV1 and RV2.

Data logger DL transmits output data from plant detection camera 1 to management personal computer (PC) of a control room within an office at a position geographically separated from the greenhouse via LAN cable LCB1 and wireless communication system RFSY. Wireless communication system RFSY is not particularly limited in communication specification, but controls communication between data logger DL within the greenhouse and management PC within the control room in the office, and furthermore transmits an instruction from management PC which relates to supply of water or fertilizer of soil spot SLP to fertilizer or water supply device WF.

Monitor 50 is connected to management PC within the control room in the office, and management PC displays output data of plant detection camera 1 that is transmitted from data logger DL on monitor 50. In FIG. 1, for example, monitor 50 displays the entirety of plant PT that is the observation target and a distribution state which relates to presence or absence of water in the entirety of plant PT. In addition, monitor 50 generates and is able to comparatively display an enlargement distribution state of a specific designated location out of the entirety of plant PT (that is, designated location ZM that is specified by a zoom operation of an observer who uses management PC) and image data corresponding to the designated location of the enlargement distribution state. Further, monitor 50, which is an example of the display unit, displays UI screen 60 including screen for monitoring water content in leaf Gm1 (refer to FIG. 14 and FIG. 15) described later.

Plant detection camera 1 has a configuration which includes visible light camera VSC and invisible light sensor NVSS. Visible light camera VSC as an example of an acquiring unit images plant PT within the greenhouse using ambient light RV0 with respect to invisible light that has a predetermined wavelength (for example, 0.4 to 0.7 μm) in the same manner as, for example, existing monitoring camera. Image data of the plant that is imaged by visible light camera VSC refers to "visible light camera image data".

Invisible light sensor NVSS incidents reference beam LS1 and measuring beam LS2 which is invisible light (for example, infrared beam) that has a plurality of types of wavelengths (refer to description below) with respect to the same plant PT as visible light camera VSC. Invisible light sensor NVSS detects presence or absence of water at the irradiation position (in other words, an area indicating individual pixels constituting a captured image of the leaf irradiated with reference beam LS1 and measuring beam LS2) of plant PT which is the observation target using the intensity ratio of diffuse reflection light RV1 and RV2 that are reflected on the irradiation position of plant PT which is radiated by reference beam LS1 and measuring beam LS2.

In addition, in visible light camera image data that is imaged by visible light camera VSC, plant detection camera 1 generates and outputs output image data (hereinafter referred to as "detection result image data") which is equivalent to the detection result of water of invisible light sensor NVSS or display data that composites information which relates to detection result image data. Display data is not limited to image data in which detection result image data and visible light camera image data are composited, and for example, may be image data that is generated such that detection result image data and visible light camera image data are able to be compared. An output destination of the display data from plant detection camera 1 is an externally connected device that is connected to plant detection camera 1 via, for example, a network, and is data logger DL or communication terminal MT (refer to FIG. 2). The network may be a wired network (for example, intranet or internet), and may be a wireless network (for example, wireless LAN).

(Description of Each Part of Plant Detection Camera)

Figure 2:
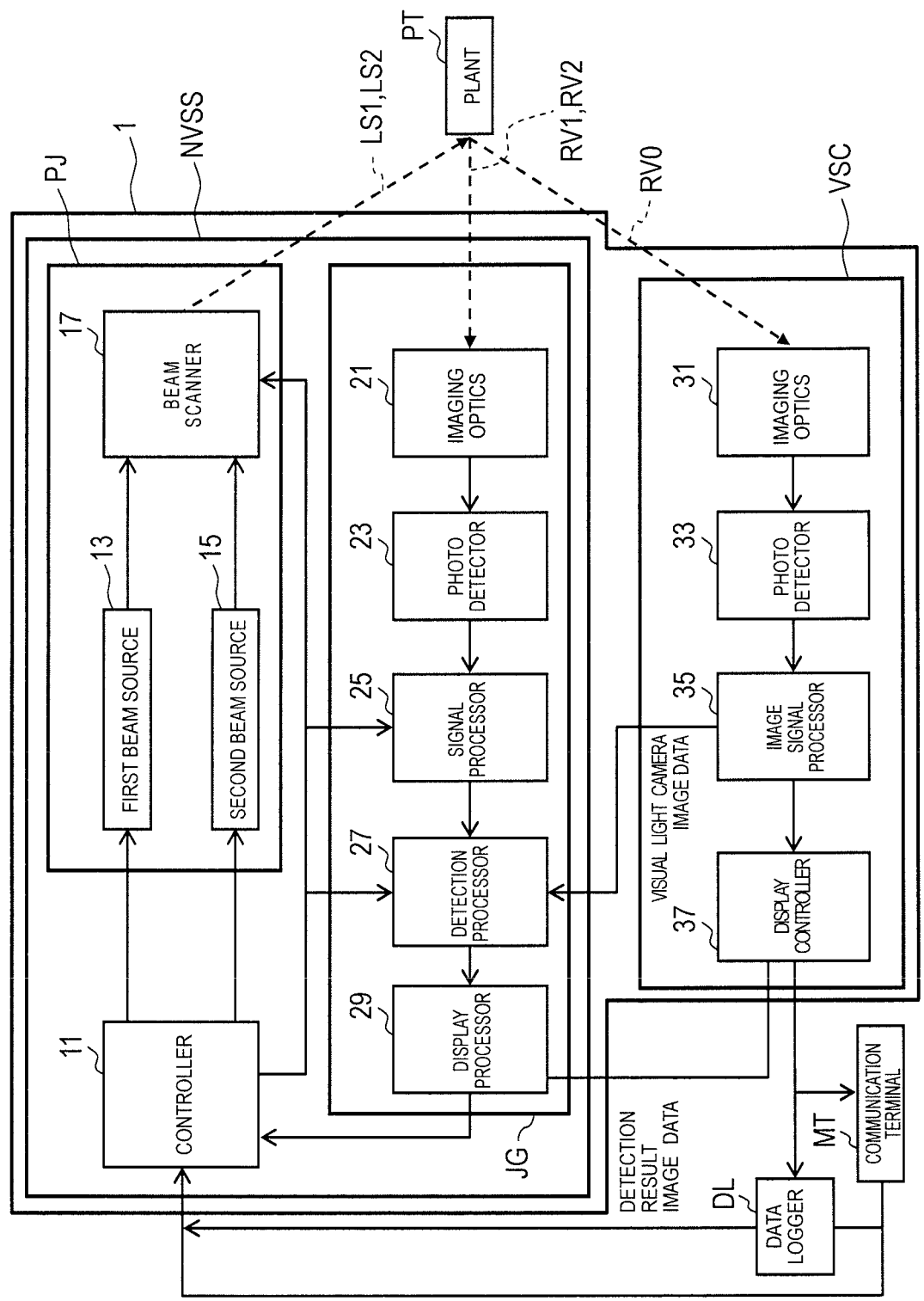
FIG. 2 is a block diagram illustrating in detail an example of an internal configuration of the plant detection camera.

FIG. 2 is a block diagram illustrating in detail an example of an internal configuration of plant detection camera 1. Plant detection camera 1 which is illustrated in FIG. 2 has a configuration which includes invisible light sensor NVSS and visible light camera VSC. Invisible light sensor NVSS has a configuration which includes controller 11, beam output PJ, and determiner JG. Beam output PJ has first beam source 13, second beam source 15, and beam scanner 17. Determiner JG has imaging optics 21, photo detector 23, signal processor 25, detection processor 27, and display processor 29. Visible light camera VSC has imaging optics 31, photo detector 33, image signal processor 35, and display controller 37. Communication terminal MT is portable by a user (for example, observer of growth of plant PT of fruit vegetable plant such as the tomato, hereinafter the same).

In the description of each part of plant detection camera 1, controller 11, invisible light sensor NVSS, and visible light camera VSC are described in order.

Controller 11 is configured using, for example, a central processor (CPU), a microprocessor (MPU), or a digital signal processor (DSP), (and also configured using, for example, a program memory and a work memory,) and performs a signal process for totally controlling an operation control of each part of visible light camera VSC and invisible light sensor NVSS, an input and output process of data within other parts, a computing process of data, and a storage process of data. In addition, controller 11 includes timing controller 11a described later (refer to FIG. 3).

Controller 11 sets detection threshold level M of plant PT which is the detection target of invisible light sensor NVSS to detection processor 27 described later. Details of the operation of controller 11 will be described later with reference to FIG. 4.

Timing controller 11a controls output of first beam source 13 and second beam source 15 in beam output PJ. In detail, timing controller 11a outputs timing signal for beam scanning TR to each of first beam source 13 and second beam source 15 in a case where light is incident to each of first beam source 13 and second beam source 15.

In addition, during the start of a predetermined incidence period, timing controller 11a alternately outputs beam output signal RF to first beam source 13 or second beam source 15. In detail, during the start of the incidence period of an odd number of times, timing controller 11a outputs beam output signal RF to first beam source 13; on the other hand, during the start of the incidence period of an even number of times, outputs beam output signal RF to second beam source 15.

Next, each part of invisible light sensor NVSS is described.

When first beam source 13 as an example of the first light source receives timing signal for beam scanning TR from timing controller 11a of controller 11, reference beam LS1 (for example, near infrared beam) that is a laser beam of invisible light that has a predetermined wavelength (for example, 905 nm) is incident on plant PT via beam scanner 17 according to beam output signal RF from timing controller 11a in each incidence period (default value) of an odd number of times.

Note that, presence or absence of detection of water in plant PT is determined by comparing to the predetermined detection threshold level M. Detection threshold level M may be a predetermined value, may be an arbitrarily set value, and furthermore, may be a value based on intensity of the diffuse reflection light that is acquired in a state in which there is no water (for example, a value in which a predetermined margin is added to a value of intensity of the diffuse reflection light that is acquired in a state in which there is no water). That is, presence or absence of detection of water may be determined by comparing detection result image data that is acquired in a state in which there is no water and detection result image data that is acquired thereafter. In this manner, it is possible to set a threshold level appropriate for an environment in which plant detection camera 1 is installed as detecting threshold level M of presence or absence of water by acquiring intensity of the diffuse reflection light in the state in which there is no water.

When second beam source 15 as an example of the second light source receives timing signal for beam scanning TR from timing controller 11a of controller 11, measuring beam LS2 (for example, infrared beam) that is the laser beam of invisible light that has a predetermined wavelength (for example, 1550 nm) is incident on plant PT via beam scanner 17 according to beam output signal RF from timing controller 11a in each incidence period (default value) of an even number of times. In the present embodiment, measuring beam LS2 that is incident from second beam source 15 is used in determination of presence or absence of detection of water in plant PT. Wavelength 1550 nm of measuring beam LS2 is a wavelength which has a characteristic in which light tends to be absorbed in water (refer to FIG. 6).

Furthermore, plant detection camera 1 detects presence or absence of water at the irradiation position of plant PT that is radiated by reference beam LS1 and measuring beam LS2 based on diffuse reflection light RV1 of reference beam LS1 as reference data for detecting water at the irradiation position of plant PT, and using diffuse reflection light RV2 at the irradiation position of plant PT that is radiated by measuring beam LS2 and diffuse reflection light RV1 of reference beam LS1. Accordingly, plant detection camera 1 is able to detect water of plant PT with high precision using reference beam LS1 and measuring beam LS2 of two types of wavelengths that detect water in plant PT differently and diffuse reflection lights RV1 and RV2 thereof.

Beam scanner 17 two-dimensionally scans reference beam LS1 which is incident from first beam source 13 and measuring beam LS2 which is incident from second beam source 15 with respect to plant PT that is present in a detection area in invisible light sensor NVSS. Thereby, plant detection camera 1 detects presence or absence of water at the irradiation position of plant PT that is radiated by reference beam LS1 and measuring beam LS2 based on diffuse reflection light RV2 that is reflected at the irradiation position of plant PT by measuring beam LS2 and diffuse reflection light RV1 described above.

Figure 3:
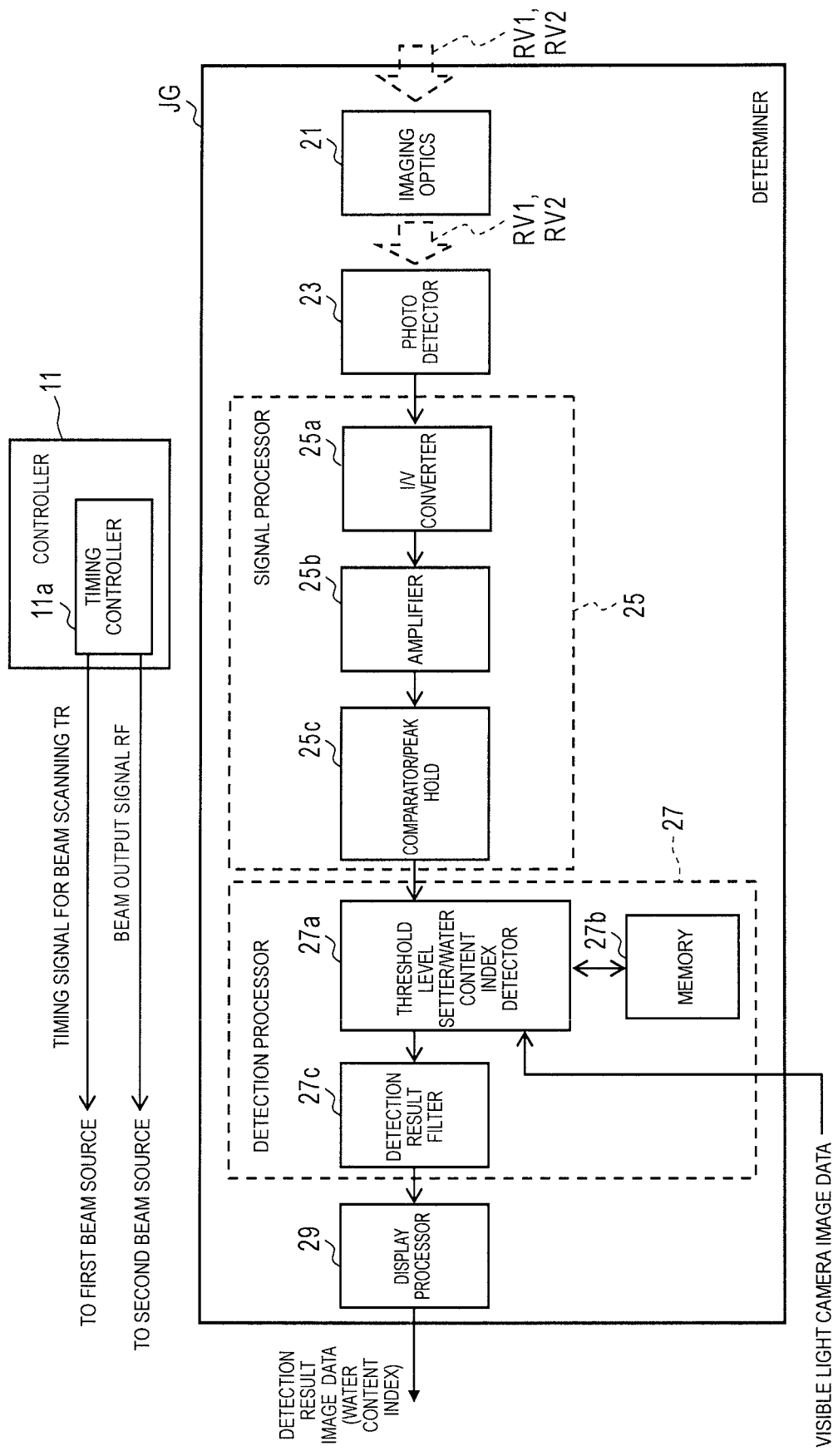
FIG. 3 is a diagram illustrating in detail an example of an internal configuration of a determiner of the plant detection camera.

Next, an internal configuration of determiner JG is described in detail with reference to FIGS. 2 and 3. FIG. 3 is a diagram illustrating in detail an example of an internal configuration of a determiner JG of plant detection camera 1.

Imaging optics 21 is configured using, for example, a single or multiple lenses, light (for example, diffuse reflection light RV1 or diffuse reflection light RV2) which is incident from outside of plant detection camera 1 is concentrated, and diffuse reflection light RV1 or diffuse reflection light RV2 form an image on a predetermined imaging area of photo detector 23.

Photo detector 23 is an image sensor which has a peak of spectral sensitivity with respect to wavelengths of both of reference beam LS1 and measuring beam LS2. Photo detector 23 converts an optical image of diffuse reflection light RV1 or diffuse reflection light RV2 that form an image on the imaging area to an electrical signal. Output of photo detector 23 is input to signal processor 25 as the electrical signal (current signal). Note that, imaging optics 21 and photo detector 23 functions as an imaging unit in invisible light sensor NVSS.

Signal processor 25 has I/V converter 25a, amplifier 25b, and comparator/peak hold 25c. I/V converter 25a converts the current signal that is an output signal (analog signal) of photo detector 23 to a voltage signal. Amplifier 25b amplifies a level of the voltage signal that is the output signal (analog signal) of I/V converter 25a up to a processable level in comparator/peak hold 25c.

Comparator/peak hold 25c binarizes the output signal of amplifier 25b and outputs to threshold level setter/water content index detector 27a according to a comparative result of the output signal (analog signal) of amplifier 25b and the predetermined threshold level. In addition, comparator/peak hold 25c includes an analog digital converter (ADC), detects and holds the peak of an analog digital (AD) converter result of the output signal (analog signal) of amplifier 25b and furthermore, outputs peak information to threshold level setter/water content index detector 27a.

Detection processor 27 has threshold level setter/water content index detector 27a, memory 27b, and detection result filter 27c. Threshold level setter/water content index detector 27a as an example of threshold holding unit generates and registers frequency distribution data in advance. Frequency distribution data indicates frequency distribution of the reflection intensity ratio (water content index) in all pixels or one frame image. As will be described later, threshold level setter/water content index detector 27a as a threshold level calculation unit is set by calculating threshold level Sh of the reflection intensity ratio for identifying the shape of the leaf using the frequency distribution data.

In addition, threshold level setter/water content index detector 27a as an example of a water detector detects presence or absence of water at the irradiation position of reference beam LS1 and measuring beam LS2 of plant PT based on output (that is, peak information) of comparator/peak hold 25c in diffuse reflection light RV1 of reference beam LS1 and output (that is, peak information) of comparator/peak hold 25c in diffuse reflection light RV2 of measuring beam LS2.

In detail, threshold level setter/water content index detector 27a temporarily stores, for example, output (that is, peak information) of comparator/peak hold 25c in diffuse reflection light RV1 of reference beam LS1 in memory 27b, and next, waits until the output (that is, peak information) of comparator/peak hold 25c in diffuse reflection light RV2 of measuring beam LS2 is obtained. Threshold level setter/water content index detector 27a obtains output (that is, peak information) of comparator/peak hold 25c in diffuse reflection light RV2 of measuring beam LS2, and then calculates a ratio of output (that is, peak information) of comparator/peak hold 25c in diffuse reflection light RV1 of reference beam LS1 and output (that is, peak information) of comparator/peak hold 25c in diffuse reflection light RV2 of measuring beam LS2 in the same line of plant PT that are contained in the angle of view with reference to memory 27b.

For example, at the irradiation position at which there is water, since a portion of measuring beam LS2 tends to be absorbed, intensity (that is, amplitude) of diffuse reflection light RV2 is attenuated. Accordingly, it is possible for threshold level setter/water content index detector 27a to detect presence or absence of water at the irradiation position of reference beam LS1 and measuring beam LS2 based on a calculation result (for example, calculation result of difference (difference ΔV of amplitude) of each intensity of diffuse reflection light RV1 and diffuse reflection light RV2 or intensity ratio of diffuse reflection light RV1 and diffuse reflection light RV2) of each line of plant PT which is contained in the angle of view.

Note that, threshold level setter/water content index detector 27a may detect presence or absence of water at the irradiation position of reference beam LS1 and measuring beam LS2 of plant PT (refer to FIG. 5) according to a comparison of the size of rate RT of amplitude difference between amplitude VA of diffuse reflection light RV1 of reference beam LS1 and amplitude VB of diffuse reflection light RV2 of measuring beam LS2 (VA−VB) and amplitude VA with predetermined detection threshold level M.

Further, threshold level setter/water content index detector 27a calculates the intensity ratio of diffuse reflection light RV1 to diffuse reflection light RV2, that is, the reflection intensity ratio (also referred to as measurement value) Ln ($I_{905}/I_{1550}$), and obtains the water content index corresponding to the water content contained in the leaf from the total sum of reflection intensity ratio Ln ($I_{905}/I_{1550}$) and an average value obtained by dividing the total sum by the number of pixel areas. In a case of assuming a visible light image of leaf PT3 as an observation target of plant detection camera 1, the pixel area is an area indicating each pixel constituting the visible light image of leaf PT3. Details of the water content index will be described below.

Reflection intensity ratio Ln ($I_{905}/I_{1550}$) is, for example, calculated by a predetermined pixel number (4×4 pixels) in all pixels in one frame imaged by visible light camera VSC, and is expressed as reflection intensity ratio W1 to Wk in each predetermined pixel number.

Memory 27b is configured using, for example, a random access memory (RAM), and temporarily stores output (that is, peak information) of comparator/peak hold 25c in diffuse reflection light RV1 of reference beam LS1.

Detection result filter 27c filters and then extracts information which relates to detection result of water from plant detection camera 1 based on output of threshold level setter/water content index detector 27a. Detection result filter 27c outputs information which relates to the detection result to display processor 29. For example, detection result filter 27c outputs information which relates to the extraction result of water at the irradiation position of reference beam LS1 and measuring beam LS2 of plant PT to display processor 29.

Display processor 29 uses output of detection result filter 27c and generates data of an invisible light image data (detection result image data) that indicates the position of water at the irradiation position at each distance from plant detection camera 1 as an example of information which relates to water at the irradiation position. Display processor 29 as an output unit outputs detection result image data which includes information on distance from plant detection camera 1 to the irradiation position to display controller 37 of visible light camera VSC. The invisible light image data does not need to include information on the distance from plant detection camera 1 to the irradiation position.

Next, each part of visible light camera VSC will be described. Imaging optics 31 is configured using, for example, a lens, ambient light RV0 from in the angle of view of plant detection camera 1 is concentrated, and ambient light RV0 forms an image on a predetermined imaging area of photo detector 33.

Photo detector 33 is an image sensor which has a peak of spectral sensitivity with respect to wavelength of visible light (for example, 0.4 to 0.7 m). Photo detector 33 converts an optical image that forms an image on the imaging surface to the electrical signal. Output of photo detector 33 is input to image signal processor 35 as the electrical signal. Note that, imaging optics 31 and photo detector 33 function as an imaging unit in visible light camera VSC.

Image signal processor 35 uses the electrical signal which is output of photo detector 33, and visible light image data is generated which is specified by a person in recognizable red, green, and blue (RGB), brightness and color difference (YUV), and the like. Thereby, visible light image data that is imaged by visible light camera VSC forms visible light camera image data. Image signal processor 35 outputs the visible light image data to display controller 37.

In a case where display controller 37 uses visible light image data that is output from image signal processor 35 and detection result image data that is output from display processor 29, and detects water at any position of the visible light image data, display data in which visible light image data and detection result image data are composited, or display data which comparatively represents the visible light image data and detection result image data are generated as examples of information related to water. Display controller 37 (output unit) prompts display by transmitting display data to data logger DL or communication terminal MT that are connected via, for example, a network.

Data logger DL transmits display data that is output from display controller 37 to communication terminal MT or one or more externally connected device (not shown), and prompts display of display data on a display screen of communication terminal MT or one or more externally connected device (for example, monitor 50 within the control room in the office indicated in FIG. 1).

Communication terminal MT is, for example, a portable communication terminal which is used by an individual user, receives display data that is transmitted from display controller 37 via the network, and displays display data on the display screen of communication terminal MT.

(Description of Example of Initial Operation in Invisible Light Sensor Controller)

Figure 4:
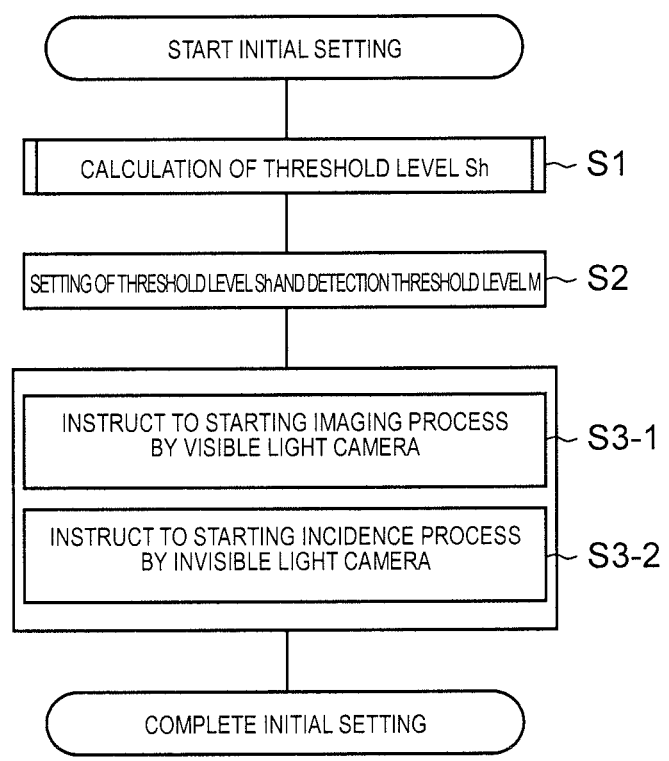
FIG. 4 is a flow chart illustrating an example of an initial setting operation in controller of the plant detection camera.

Next, an example of an initial operation in controller 11 of invisible light sensor NVSS of plant detection camera 1 of the present embodiment will be described with reference to FIG. 4. FIG. 4 is a flow chart illustrating an example of an initial setting operation in controller 11 of plant detection camera 1.

When controller 11 instructs settings of threshold level Sh of reflection intensity ratio for identifying the shape of the leaf with respect to threshold level setter/water content index detector 27a, threshold level setter/water content index detector 27a calculates and sets threshold level Sh (S1). Details of the process in which threshold level Sh is set will be described below. Note that, in a case where threshold level Sh is a fixed value, the process of step S1 may be omitted.

In addition, controller 11 sets detection threshold level M of water in detection processor 27 of invisible light sensor NVSS in threshold level setter/water content index detector 27a (S2). It is preferable to appropriately provide detection threshold level M according to a specific substance that is a detection target.

After the process of step S2, controller 11 outputs a control signal for starting an imaging process to each part of visible light camera VSC (S3-1) and outputs to first beam source 13 and second beam source 15 of invisible light sensor NVSS timing signal for beam scanning TR for starting incidence of reference beam LS1 and measuring beam LS2 to first beam source 13 and second beam source 15 (S3-2). Note that, either an execution timing of an operation of step S3-1 or an execution timing of an operation of step S3-2 may be first, or may be simultaneous.

Figure 5:
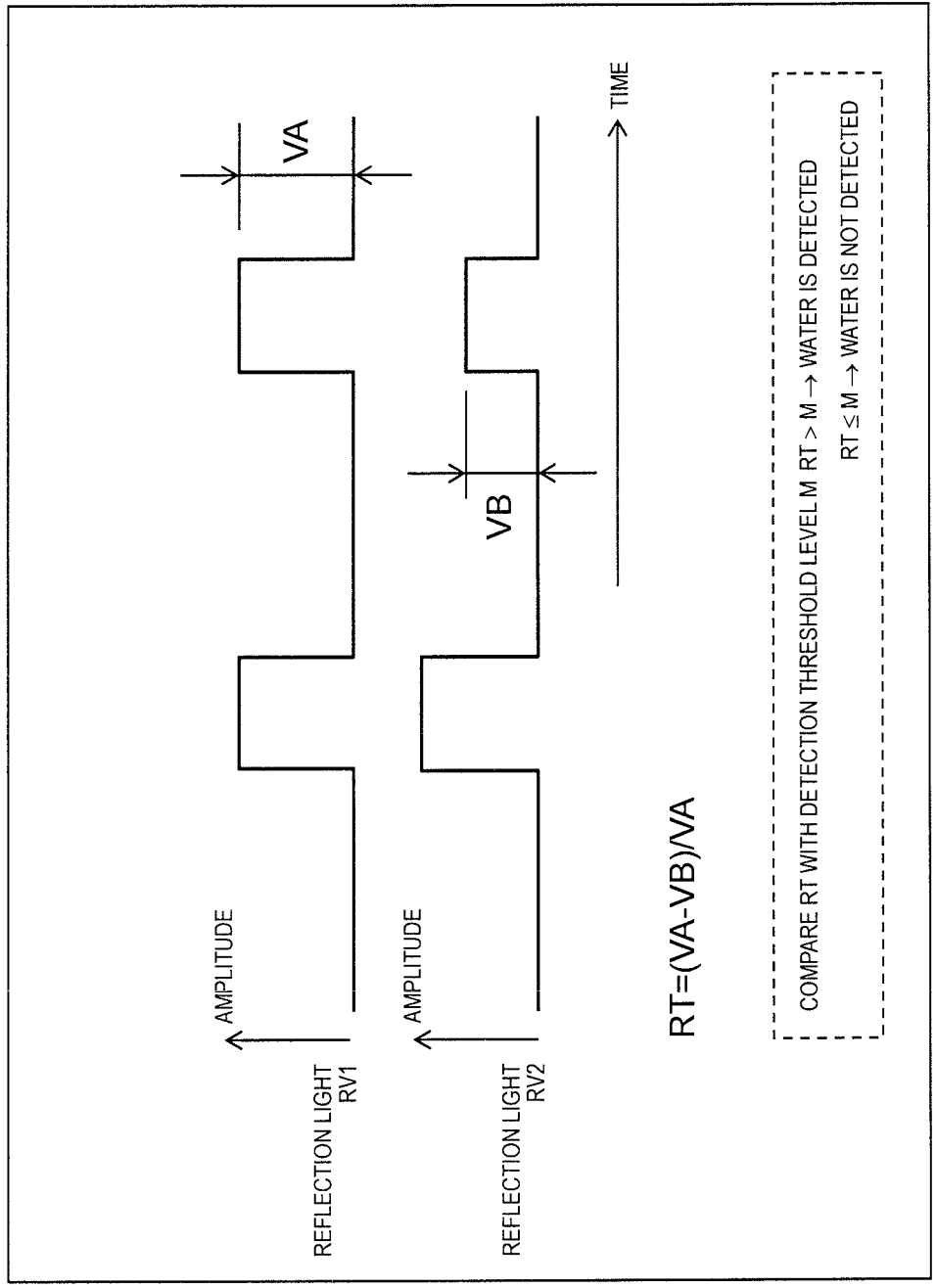
FIG. 5 is a principle explanatory diagram of detection of water in invisible light sensor.

FIG. 5 is a principle explanatory diagram of detection of water in invisible light sensor NVSS. For example, threshold level setter/water content index detector 27a may determine that water is detected if RT>M, and may determine that water is not detected if RT≤M. In this manner, threshold level setter/water content index detector 27a is able to eliminate influence of noise (for example, disturbance light) and is able to detect presence or absence of water with high precision by detecting presence or absence of water according to a comparative result of rate RT between amplitude difference (VA−VB) and amplitude VA and detection threshold level M.

Figure 6:
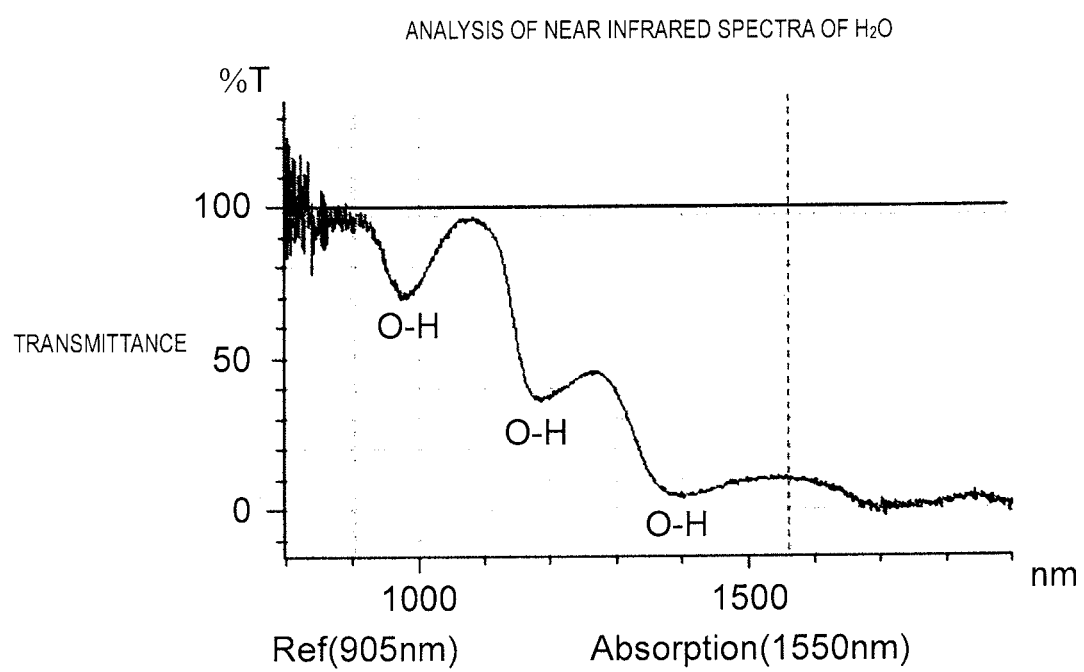
FIG. 6 is a graph illustrating an example of the near infrared spectra of water ($H_2O$).

FIG. 6 is a graph illustrating an example of the near infrared spectra of water ($H_2O$). A horizontal axis of FIG. 67 indicates wavelength (nm), and a vertical axis of FIG. 6 indicates transmittance (transparency) (%). As illustrated in FIG. 6, since reference beam LS1 of wavelength 905 nm has transmittance in water ($H_2O$) that is close to 100%, it is understood that reference beam LS1 has a characteristic of which light tends not to be absorbed in water. In the same manner, since measuring beam LS2 of wavelength 1550 nm has transmittance in water ($H_2O$) that is close to 10%, it is understood that measuring beam LS2 has a characteristic of tending to be absorbed in water. Therefore, in the present embodiment, the wavelength of reference beam LS1 which is incident from first beam source 13 is 905 nm, and the wavelength of measuring beam LS2 which is incident from second beam source 15 is 1550 nm.

Even in a case where the projection range of the near infrared beam is decreased as the leaf withers, or the leaf is warped or rolled up to increase the thickness of the leaf, in the present embodiment, an average value (pixel average value) (hereinafter, referred to as "pixel average water content index") obtained by dividing a total sum of the reflection intensity ratio in all the pixel areas (that is, each pixel) constituting the invisible light image of the leaf by the number of pixels, and a total sum (hereinafter, referred to as "total sum of the water content index") for each pixel of the reflection intensity ratio in all the pixels constituting the invisible light image of the leaf by the number of pixels are used as indexes of the water content. Further, a value of the pixel average water content index when water stress is not applied (that is, at an initial stage) and a value of the total sum of the water content index each of which are normally indicated as 1.0 are also referred to as a standardized pixel average water content index and a total sum of the standardized water content index. In this way, by expressing the initial value as 1.0 with relative value, it is possible to easily perform relative comparison of temporal changes of "pixel average water content index" and "total sum of the water content index" of leaves having different angle and leaf thickness. These pixel average water content index and the total sum of the water content index are calculated by using the reflection intensity ratio calculated for each pixel constituting the invisible light image of the leaf. Accordingly, the pixel average water content index is represented by "(1/number of pixels constituting invisible light image of leaf)×Σ Ln ($I_{905}/I_{1550}$)", the total sum of the water content index is represented by "Σ Ln ($I_{905}/I_{1550}$)", and both have a strong correlation with the water potential (in other words, the application amount of water stress). Note that, all the pixel areas constituting the invisible light image of the leaf are, for example, a set of areas where the pixel value (that is, the value of the reflection intensity ratio in the pixels corresponding to the positions where reference beam LS1 and measuring beam LS2 are radiated) is greater than threshold level Sh at the beginning of the measurement period. Note that, threshold level Sh may be a predetermined value, or may be calculated by using a method illustrated in FIG. 19 described below.

(Description of Detailed Operation Relating to Detection of Water and Undulation of Invisible Light Sensor)

Figure 7:
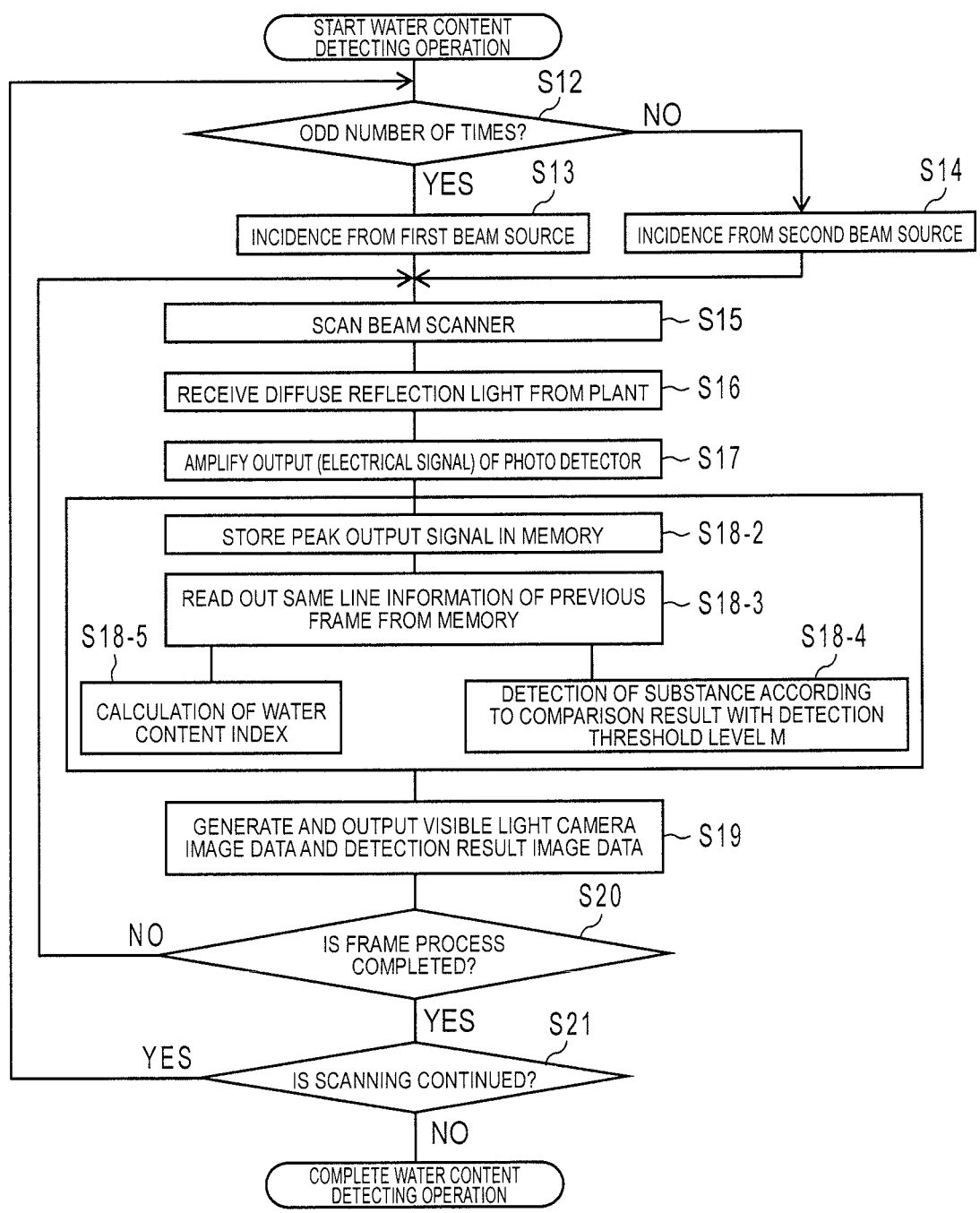
FIG. 7 is a flow chart illustrating a detailed operation procedure which relates to detection of water that is contained in a leaf of a plant in an invisible light sensor.

Next, a detailed operation procedure which relates to detection of water in invisible light sensor NVSS of plant detection camera 1 will be described with reference to FIG. 7. FIG. 7 is a flow chart illustrating a detailed operation procedure which relates to detection of water that is contained in leaf PT3 of plant PT in invisible light sensor NVSS. As a premise of description of the flow chart illustrated in FIG. 7, timing controller 11a outputs timing signal for beam scanning TR to first beam source 13 and second beam source 15, and reference beam LS1 or measuring beam LS2 from plant detection camera 1 is radiated toward leaf PT3 of plant PT.

In FIG. 7, controller 11 determines whether or not beam output signal RF in incidence period of an odd number of times is output from timing controller 11a (S12). In a case where controller 11 determines that beam output signal RF in incidence period of an odd number of times is output from timing controller 11a (YES in S12), first beam source 13 incidents reference beam LS1 according to beam output signal RF from timing controller 11a (S13). Beam scanner 17 one-dimensionally scans reference beam LS1 of one line or more in an X direction of plant PT which is contained in the angle of view of plant detection camera 1 (S15). At the irradiation position on each line in the X direction on which the reference beam LS1 is radiated, diffuse reflection light RV1 that is generated by reference beam LS1 being diffused and reflected is received by photo detector 23 via imaging optics 21 (S16).

In signal processor 25, output (electrical signal) in photo detector 23 of diffuse reflection light RV1 is converted to the voltage signal, and the level of the electrical signal is amplified up to a processable level in comparator/peak hold 25c (S17). Comparator/peak hold 25c binarizes the output signal of amplifier 25b and outputs to threshold level setter/ water content index detector 27a according to a comparative result of the output signal of amplifier 25b and the predetermined threshold level. Comparator/peak hold 25c outputs peak information of output signal of amplifier 25b to threshold level setter/water content index detector 27a.

Threshold level setter/water content index detector 27a temporarily stores output (that is, peak information) of comparator/peak hold 25c with respect to diffuse reflection light RV1 of reference beam LS1 in memory 27b (S18-2). In addition, threshold level setter/water content index detector 27a reads from memory 27b output of comparator/peak hold 25c with respect to the same line in diffuse reflection light RV1 or diffuse reflection light RV2 with respect to reference beam LS1 or measuring beam LS2 in a previous frame (incidence period) that is stored in memory 27b (S18-3).

Threshold level setter/water content index detector 27a detects presence or absence of water on the same line based on output (that is, peak information) of comparator/peak hold 25c in diffuse reflection light RV1 of reference beam LS1 and output (that is, peak information) of comparator/peak hold 25c in diffuse reflection light RV2 of measuring beam LS2 on the same line and predetermined detection threshold level M (S18-4).

Threshold level setter/water content index detector 27a calculates a water content index which is a total sum Σ Ln ($I_{905}/I_{1550}$) of the reflection intensity ratio (S18-5). Details of calculation of the water content index will be described below.

Display processor 29 uses output of detection result filter 27c and generates detection result image data that indicates the detection position of water. Display controller 37 outputs detection result image data that is generated by display processor 29 and visible light camera image data of a visible light image that is imaged by visible light camera VSC (S19). Each operation of steps S15, S16, S17, S18-2 to S18-5, and S19 is executed in each line within the detection area of one frame (incidence period).

That is, when each operation of steps S15, S16, S17, S18-2 to S18-5, and S19 is completed with respect to one line in the X direction, each operation of steps S15, S16, S17, S18-2 to S18-5, and S19 is performed with respect to a subsequent line in the X direction (NO in S20). Thereafter, when each operation of steps S15, S16, S17, S18-2 to S18-5, and S19 for one frame is completed, each operation of steps S15, S16, S17, S18-2 to S18-5, and S19 is repeatedly performed.

Meanwhile, in a case where execution of each operation of steps S15, S16, S17, S18-2 to S18-5, and S19 is complete with respect to all lines in one frame (YES in S20), and in a case where scanning of incident light is continued (YES in S21), an operation of invisible light sensor NVSS returns to step S12. Meanwhile, in a case where scanning of reference beam LS1 and measuring beam LS2 is not continued (NO in S21), the operation of invisible light sensor NVSS is complete.

Figure 8:
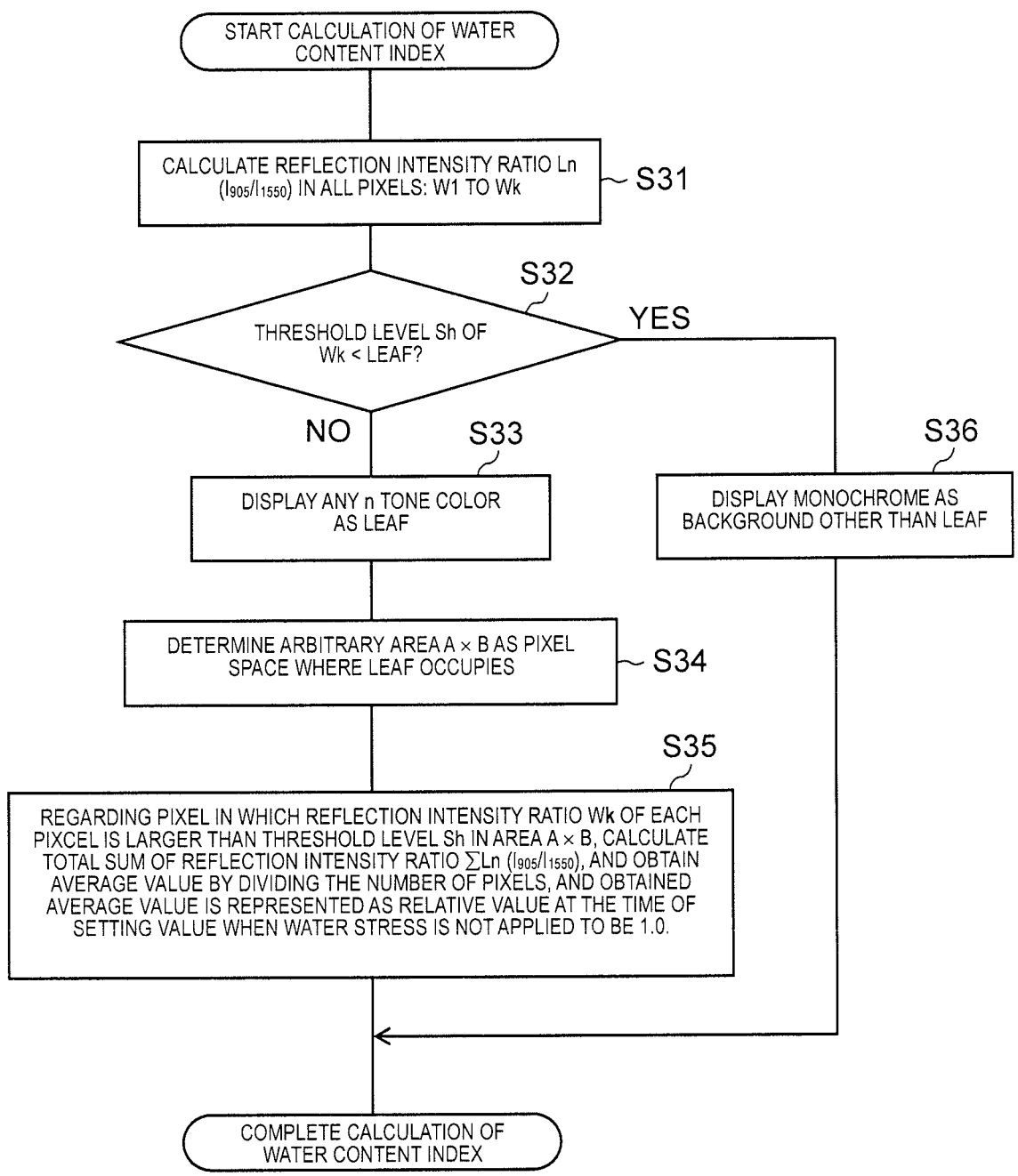
FIG. 8 is a flow chart illustrating a calculation procedure of a water content index in step S18-5.

FIG. 8 is a flow chart illustrating a calculation procedure of a water content index in step S18-5. Threshold level setter/water content index detector 27a calculates the reflection intensity ratio of Σ Ln ($I_{905}/I_{1550}$) in all pixels from the frame image (S31). Here, a measurement value of reflection intensity ratio Ln ($I_{905}/I_{1550}$) of each pixel is represented by reflection intensity ratios W1 to Wk. For example, in a case where the image of the near infrared beam is configured from 76,800 (=320×240) pixels, a suffix k of Wk is a variable which represents 1 to 76,800.

Threshold level setter/water content index detector 27a determines whether or not a pixel value (that is, reflection intensity ratio Wk) for each pixel is larger than threshold level Sh for identifying leaf PT3 (S32). An initial value of threshold level Sh is registered in advance in threshold level setter/water content index detector 27a as an empirical value. The empirical value is determined according to a specification of the device for observing water content (intensity of the irradiation laser beam, sensitivity of a light receiving element, and the like), water content (approximately 90%) of the leaf that is the measurement target, thickness of the leaf (for example, 200 μm), inside/outside (or "indoor/outdoor"), and the like. In particular, in a case of outside, there is change according to how sunlight hits or manner of growth of foliage, and the variable is changed each time.

For example, as the empirical value, in the case of an imaging distance of 1 m, threshold level Sh during imaging inside is set to approximately 0.3. Threshold level Sh during imaging outside is set to approximately 0.9. In addition, in the case of an imaging distance of 3 m, threshold level Sh during imaging inside is set to approximately 0.05. It is preferable to change threshold level Sh in a case where threshold level Sh is set as the initial value, it is determined whether or not the threshold level is optimal in comparison to the actual shape of the leaf, and the threshold level is not optimal. In addition, as will be described later, a calculation process of threshold level Sh is performed, and it is possible to register calculated threshold level Sh as the initial value.

In step S32, in a case where reflection intensity ratio Wk is less than threshold level Sh, the pixel is a pixel (in other words, pixels that are not pixels constituting the visible light image area regarded as a leaf) that represents a background other than the leaf, and display processor 29 generates monochromatic display data for displaying pixels monochromatically (S36).

Meanwhile, in step S32, in a case where reflection intensity ratio Wk is threshold level Sh or more (threshold level or more), display processor 29 displays pixels in a tone color corresponding to reflection intensity ratio Ln ($I_{905}/I_{1550}$) (S33). Here, it is possible to display the tone color corresponding to reflection intensity ratio Ln ($I_{905}/I_{1550}$) at n tone. n is an arbitrary positive number.

In detail, in a case where reflection intensity ratio Ln ($I_{905}/I_{1550}$) is less than 0.3, that is, in a case of being threshold level Sh of the leaf or less, the pixel is displayed using, for example, white (monochrome). Meanwhile, in a case where reflection intensity ratio Ln ($I_{905}/I_{1550}$) is 0.3 to less than 0.4, the pixel is displayed using, for example, dark green. In the same manner, in a case of being 0.4 to less than 0.5, the pixel is displayed using green. In a case of being 0.5 to less than 0.55, the pixel is displayed using yellow. In a case of being 0.55 to less than 0.6, the pixel is displayed using orange. In a case of being 0.6 to less than 0.75, the pixel is displayed using red. In a case of being 0.75 or more, the pixel is displayed using purple. In this manner, the color of the pixel that belongs to the leaf is set in any of six tones.

Note that, in a case where a pixel space which the leaf occupies is not appropriate in comparison to the actual shape of the leaf, the user may set threshold level Sh up or down in each predetermined increment (for example, 0.01). Alternatively, the user may set appropriate threshold level Sh by activating a process in which threshold level Sh described later is automatically set.

Threshold level setter/water content index detector 27a specifies an area of the pixel space which the leaf occupies (S34). The pixels of the leaf are pixels in which reflection intensity ratio Ln ($I_{905}/I_{1550}$) exceeds threshold level Sh (here, 0.3). In addition, an area ARE of a rectangle (A×B) is specified such that the pixels of the leaf are enclosed. The area ARE is used as a value which determines the size of the leaf Note that, the size of the leaf may represent the pixel number which exceeds threshold level Sh.

Threshold level setter/water content index detector 27a as an example of a water content calculation unit (water content calculation unit) calculates the water content index $\Sigma$ Ln ($I_{905}/I_{1550}$) that is a total sum of reflection intensity ratio Ln ($I_{905}/I_{1550}$) where a measurement value (reflection intensity ratio Ln ($I_{905}/I_{1550}$)) is larger than threshold level Sh in area ARE (S35). The water content which is contained in the entirety of the leaf is understood by obtaining water content index $\Sigma$ Ln ($I_{905}/I_{1550}$).

Furthermore, in step S35, it is possible for threshold level setter/water content index detector 27a to calculate the number of pixels in which the measurement value (reflection intensity ratio Ln ($I_{905}/I_{1550}$)) is larger than threshold level Sh in area ARE, and calculate an average value by dividing total sum $\Sigma$ Ln ($I_{905}/I_{1550}$) of the reflection intensity ratio by the number of calculated pixels. The average value is a value in which the total sum of the reflection intensity ratio is divided by the area of the leaf where the external form of the leaf is determined by threshold level Sh. The average value is different from a value in which the total sum of the reflection intensity ratio in a spot is divided by a fixed area of the spot, and is different from a value obtained by dividing the total sum of the reflection intensity ratios by the area surrounded by the outline of the leaf in the visible image. After this, the calculation operation of the water content index ends.

In this manner, in the present embodiment, the reflection intensity ratio of each irradiation position is not obtained, the reflection intensity ratio of each pixel in the frame image is obtained, and it is possible to correctly calculate the water content index from the total sum of reflection intensity ratio of each pixel. Accordingly, it is possible to accurately determine status of the leaf, that is, the plant.

Figure 18A:
FIG. 18A is a diagram illustrating a frame image that images stalks and leaves of a tomato.
Figure 18B:
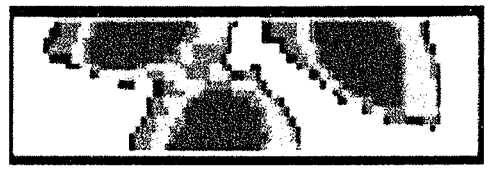
FIG. 18B is a diagram illustrating the occupancy space of the leaf which is obtained in a case where the imaging distance is set to 3 m and a threshold level is set to 0.05 with respect to the visible light image in FIG. 18A.
Figure 18C:
FIG. 18C is a diagram illustrating the occupancy space of the leaf which is obtained in a case where the imaging distance is set to 1 m and a threshold level is set to 0.3 with respect to the visible light image in FIG. 18A.

Here, as described above, threshold level Sh of the leaf is set to a subsequent value as the initial value. In a case where plant detection camera 1 is installed inside and leaf PT3 is imaged inside, and in a case where imaging distance is empirically 1 m, threshold level Sh is set to approximately 0.3. In the case of an imaging distance of 3 m, threshold level Sh is set to approximately 0.05. Meanwhile, in a case of imaging outside, since a condition is fluctuated, threshold level Sh is empirically set to approximately 0.9. FIGS. 18A to 18C are diagrams illustrating an occupancy range of the leaf. FIG. 18A is a frame image that images stalks and leaves of a tomato. A distance between leaves is approximately 1 cm. FIG. 18B illustrates the occupancy space of the leaf which is obtained in a case where the imaging distance is set to 3 m and threshold level Sh is set to 0.05 with respect to the visible light image in FIG. 18A. In this case, it is understood that the leaves overlap in portions and threshold level Sh (=0.05) is a value that is inappropriately set. FIG. 18C illustrates the occupancy space of the leaf which is obtained in a case where the imaging distance is set to 1 m and threshold level Sh is set to 0.3 with respect to the visible light image in FIG. 18A. In this case, the outer form of the leaf does not overlap with another leaf, in addition, the occupancy space of the leaf is the same as the size of the outer form of the leaf of the visible light image. In this case, it is understood that threshold level Sh (=0.3) is a value that is correctly set.

Figure 19:
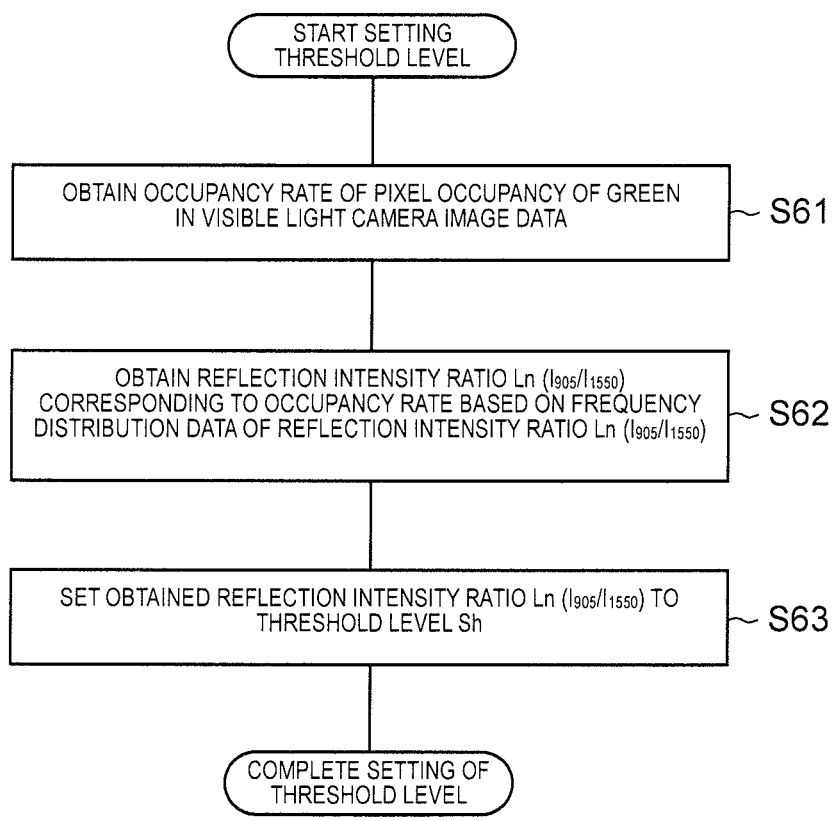
FIG. 19 is a flow chart illustrating a threshold level setting procedure.

In addition, threshold level Sh of the leaf may not be registered before the subsequent process is performed and the calculation process of the water content index indicated in FIG. 8 is executed. FIG. 19 is a flow chart illustrating a threshold level setting procedure.

Threshold level setter/water content index detector 27a obtains an occupancy rate that is determined as the leaf (G pixel number/all pixel numbers), i.e. a pixel occupancy of green (G) that is determined as the color of the leaf with respect to the frame image (for example, refer to FIG. 18A) that is imaged by visible light camera VSC (S61).

Figure 20:
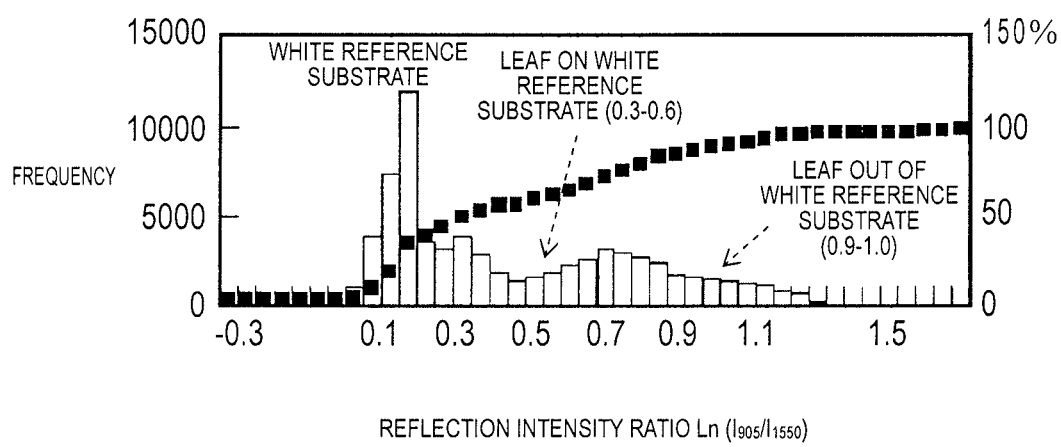
FIG. 20 is a graph illustrating frequency distribution of a reflection intensity ratio in all pixels.

Threshold level setter/water content index detector 27a obtains the water content index corresponding to the occupancy rate of the leaf based on frequency distribution data of the water content index (S62). FIG. 20 is a graph illustrating the frequency distribution of the reflection intensity ratio in all pixels. Frequency distribution data is registered in threshold level setter/water content index detector 27a. When using the frequency distribution data, in a case where, for example, the occupancy rate that is determined as the pixel occupancy of green (G) that is determined as the color of the leaf is 52%, the water content index is approximately 0.3.

Threshold level setter/water content index detector 27a sets the water content index that is obtained in step S62 to threshold level Sh (S63). After this, threshold level setter/water content index detector 27a ends the present process.

In this manner, it is possible to correctly determine the outer form of the leaf by obtaining an occupancy pixel number of green (specified color) of the leaf and threshold level Sh corresponding to cumulative frequency of Ln ($I_{905}/I_{1550}$) that is the measurement value which is the same pixel number by utilizing the visible light image that is imaged by visible light camera VSC, that is, by modifying the threshold level of the water content of each pixel that is contained in the leaf. Accordingly, it is possible to accurately calculate the average value of the pixel unit by correctly determining the outer form of the leaf. In contrast to this, in a case where the fixed area of the spot or the outer form of the visible light image is used, when the outer form of the leaf is not correctly captured, a large error is generated in the average value of the pixel unit.

Figure 9:
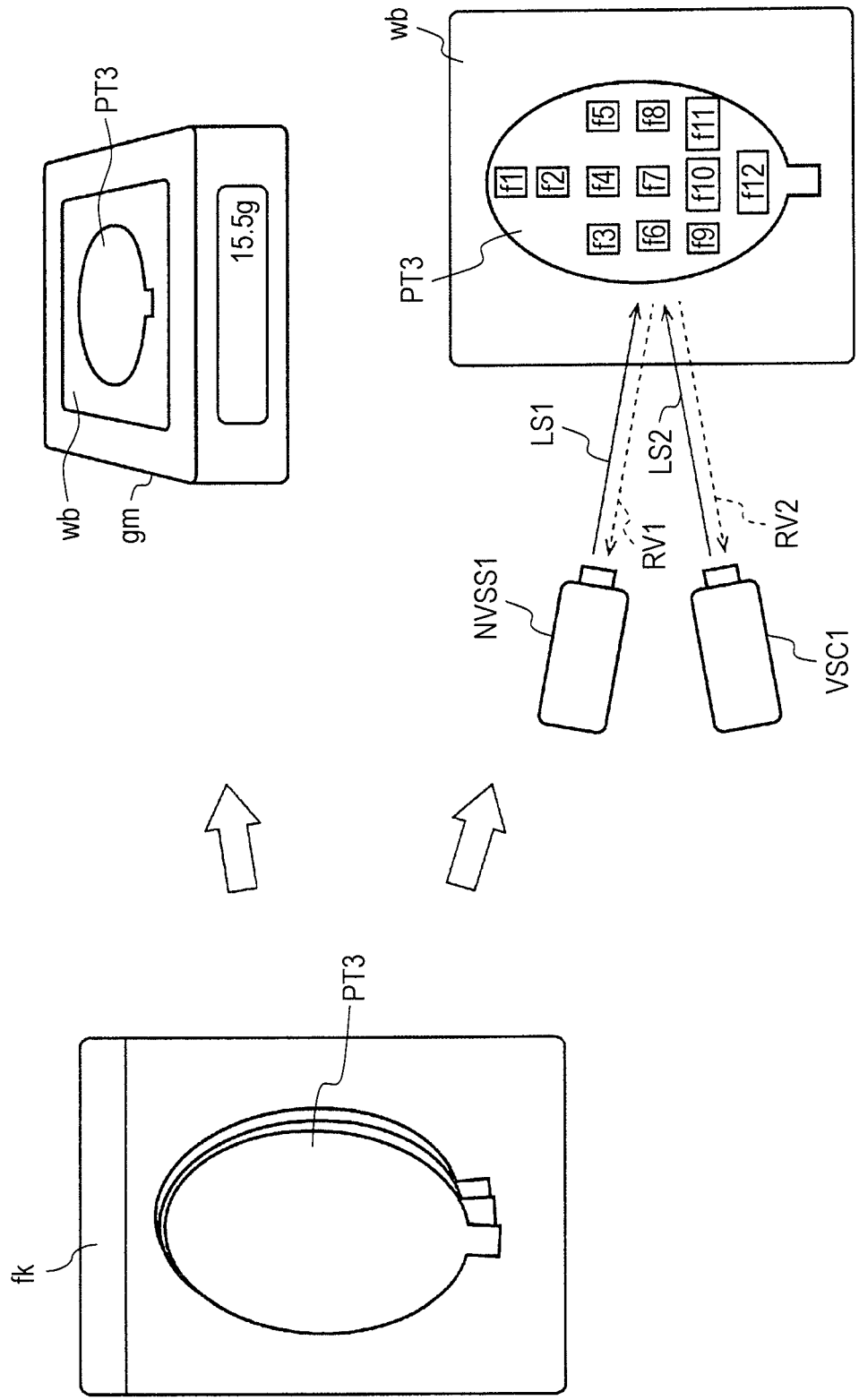
FIG. 9 is a diagram illustrating an example of the method of measuring Comparative Examples.

Here, Comparative Examples will be described for another method of measuring the water content in the leaf. FIG. 9 is a diagram illustrating an example of the method of measuring Comparative Examples. Macrophyll leaf PT3 that is sealed and packed in vinyl bag fk is taken out and fixed to white board wb such that leaf PT3 does not move. White board wb that is firmly fixed to leaf PT3 is placed on weight scale gm, and the weight is measured. At this time, since the weight of white board wb is measured in advance, and is adjusted by 0 points, the weight of the leaf is displayed on a meter of weight scale gm. Change of weight due to transpiration of the leaf is measured while the time elapses. After all measurement ends, the leaf completely dries and the weight is obtained. The average water content of the leaf during measurement is obtained by deducting the weight of the leaf during drying from the weight of the leaf during measurement. The average water content of the leaf substantially lowers while the time elapses.

On the other hand, in the present embodiment, at the time of measuring the water content of the leaf, a background material is disposed so as to cover a back surface (rear side) of the leaf that is the measurement target. As the material of the background material, a material that does not contain water and that does not deform due to pesticide, sprinkling, or $CO_2$ spraying is given such as plastic, coated paper, sheets such as aluminum foil (plate), a plate, or a block. In addition, it is desirable that the size of the background material has a large surface such that the leaf that is the measurement target is covered and is a size so as not to interfere with photo-synthesis of another leaf within two times the projection area of the leaf that is the measurement target. In addition, it is preferable that the thickness of the background material is a thickness of 50 m to 1 mm self-supporting without curling, and in particular, 50 to 200 μm. In addition, in a case of being supported by the stalk of the leaf, it is preferable that the weight of the background material is a weight to a degree that the leaf does not wilt. In addition, it is preferable that the color of the background material is white or silver with high reflectance of visible light and the near infrared beam.

In the present embodiment, as the background material, a case of using a white reference substrate is indicated. Note that, a white plastic plate, an aluminum plate, a standard white plate, white paper, and the like are given as the white reference substrate.

Figure 10A:
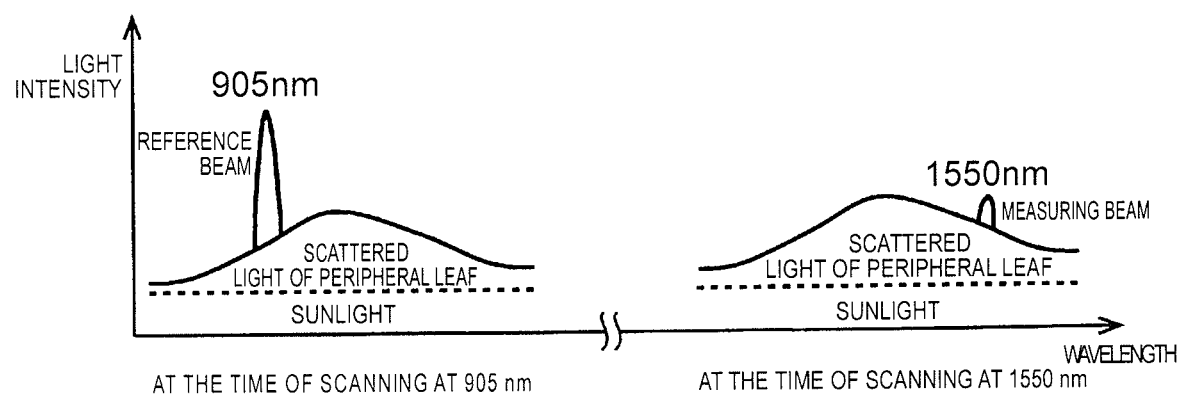
FIG. 10A is a graph illustrating an example of the reflection light intensity with respect to wavelength of the near infrared beam when near infrared beam is radiated toward the leaf outdoor.

FIG. 10A is a graph illustrating an example of the reflection light intensity with respect to wavelength of the near infrared beam when near infrared beam is radiated toward the leaf outdoors. The vertical axis indicates intensity of the near infrared light which is detected by invisible light sensor NVSS, and the horizontal axis indicates wavelength of a near infrared area. Intensity of light that is scattered by the peripheral leaf other than intensity of light according to sunlight is included in intensity of the near infrared light which is detected by invisible light sensor NVSS. That is, a rise of the background due to multiple scattering of sunlight being carried out on the peripheral leaf is included in the intensity of the detected near infrared light. In addition, intensity of light detected by invisible light sensor NVSS is small due to the near infrared beam which has a wavelength of 1550 nm being absorbed by the peripheral leaf. Accordingly, the value of reflection intensity ratio Ln ($I_{905}/I_{1550}$) is large. Therefore, in a case where water content of the leaf outside is measured, it is necessary to set the value of threshold level Sh that is compared to reflection intensity ratio Ln ($I_{905}/I_{1550}$) to be large.

Figure 10B:
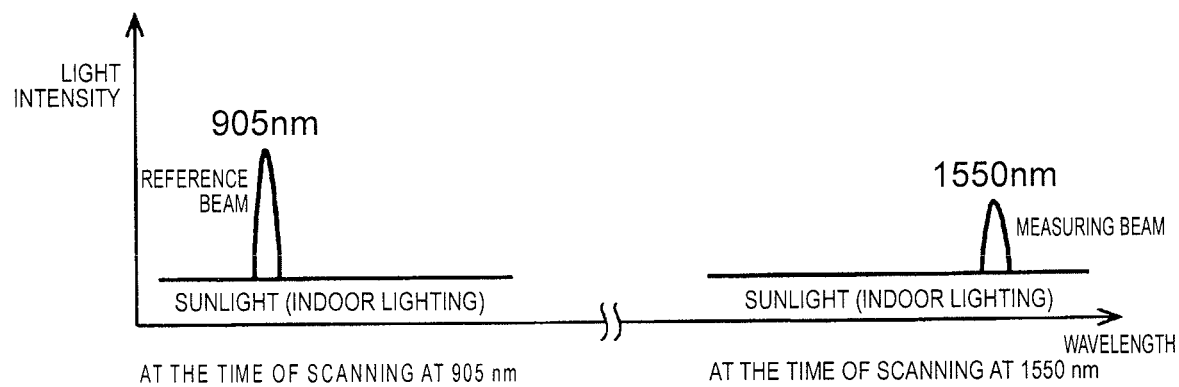
FIG. 10B is a graph illustrating an example of the reflection light intensity with respect to wavelength of the near infrared beam when near infrared beam is radiated toward the leaf on which white reference substrate bd is installed indoors and outdoors.

FIG. 10B is a graph illustrating an example of the reflection light intensity with respect to wavelength of the near infrared beam when near infrared beam is radiated toward the leaf on which white reference substrate bd is installed indoors and outdoors.

The vertical axis indicates intensity of the near infrared light which is detected by invisible light sensor NVSS, and the horizontal axis indicates wavelength of a near infrared area. Multiple scattering from the leaf surrounding leaf PT3 that is a measurement target does not occur due to white reference substrate bd being disposed to cover the back surface (rear side) of leaf PT3t that is the measurement target. Accordingly, a lowering of intensity of the near infrared beam which has a wavelength of 1550 nm does not occur. In addition, in the case of inside, a rise of the background does not occur. Note that, in a case of measuring outside, threshold level Sh is set to approximately 0.5. In addition, in a case of measuring inside, threshold level Sh is set to approximately 0.3.

In a case where white reference substrate bd is disposed on the back surface of leaf PT3t that is the measurement target, the leaf may be disposed without being fixed, and leaf PT3t may be attachably fixed to white reference substrate bd. Here, a case where leaf PT3t is attached to white reference substrate bd is illustrated. In each embodiment including the present embodiment, as seen from first beam source 13 and second beam source 15 of plant detection camera 1, white reference substrate bd is disposed on the back of at least one leaf that is the measurement target.

FIG. 11 is a diagram which describes an example of attachment of leaf PT3t on white reference substrate bd. White reference substrate bd is a white plastic plate which has a vertical rectangular shape. Aperture bd1 that is hollowed out in a rectangular shape is formed in the center of white reference substrate bd. In addition, round hole bd2 is formed in an upper portion of white reference substrate bd. Slit bd21 which reaches up to an upper end surface is formed on hole bd2. In addition, three slits bd3, bd4, and bd5 are respectively formed on the lower side and both sides of aperture bd1 that is formed on white reference substrate bd.

In a case where leaf PT3t is attached to white reference substrate bd, a tip end of leaf PT3t is inserted into one of three slits bd3, a void is generated by shifting horizontal white reference substrate bd in a longitudinal direction centered on slit bd21, stalk PT2 of the leaf passes inside, and stalk PT2 is fixed to hole bd2.

Next, control experiment for the water potential (in other words, application of water stress) contained in leaf PT3 is performed as the observation of the water content contained in leaf PT3 of plant PT by using plant detection camera 1 of the present embodiment, and the activity in the leaf due to the water stress obtained by the result of the experiment is considered.

Figure 12:
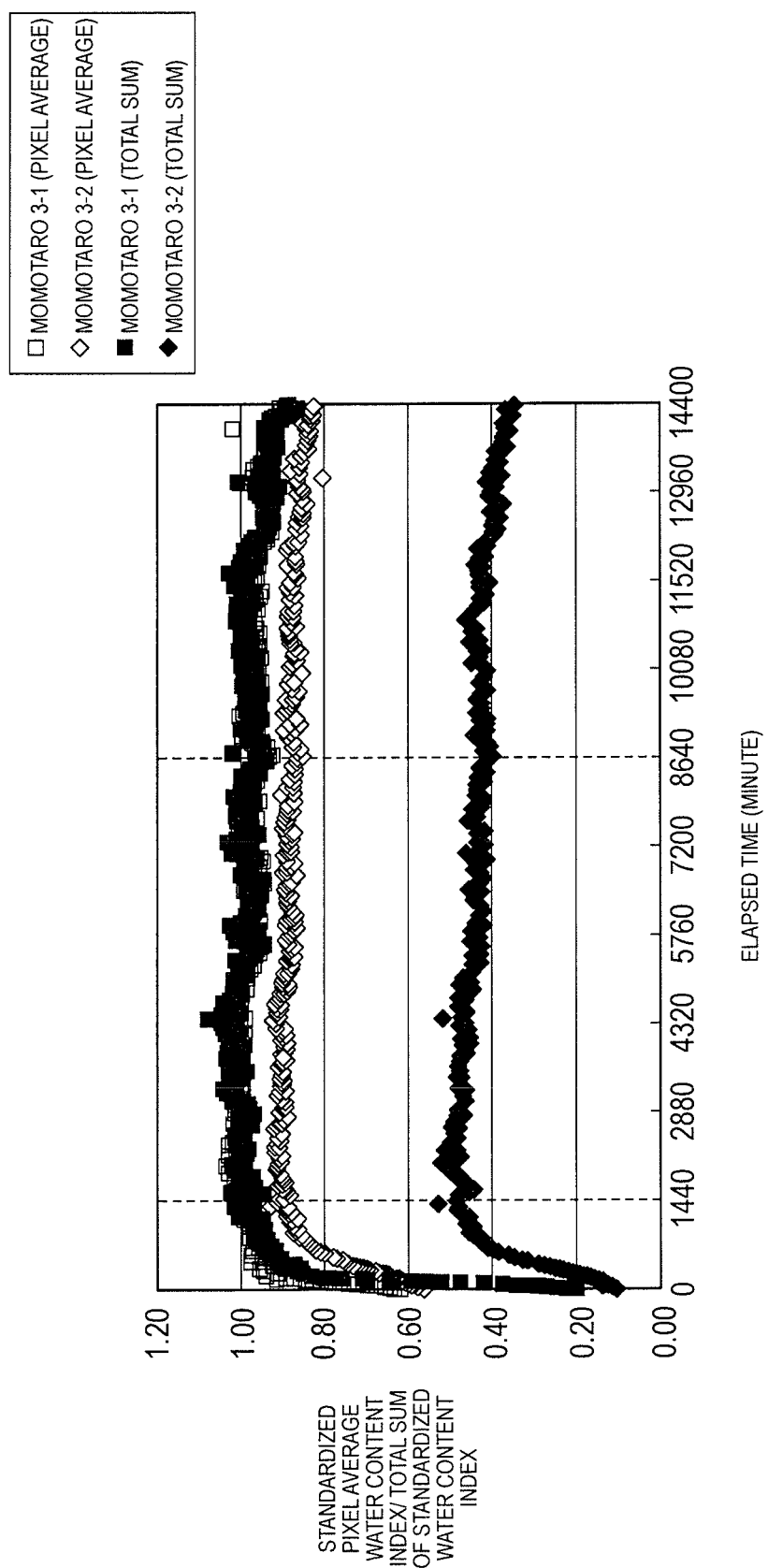
FIG. 12 is a graph illustrating an example of a time-transition of a standardized pixel average water content index and a total sum of the standardized water content index in a water potential control experiment.
Figure 13:
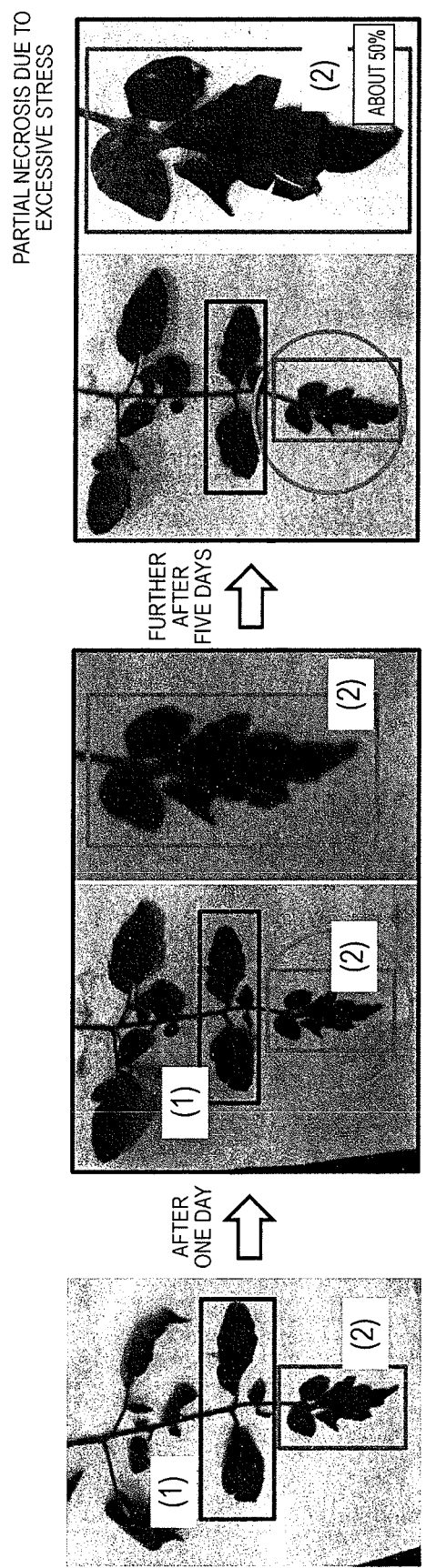
FIG. 13 is a diagram illustrating an example of a state of a leaf of "Momotaro 3-2" to which water stress is applied at a first day in FIG. 12, one day after the first day, and six days after the first day.

FIG. 12 is a graph illustrating an example of a time change of a standardized pixel average water content index and a total sum of the standardized water content index in a water potential control experiment. FIG. 13 is a diagram illustrating an example of a state of a leaf of "Momotaro 3-2" to which water stress is applied at a first day in FIG. 12, one day after the first day, and six days after the first day. The vertical axis of the graph in FIG. 12 indicates a standardized pixel average water content index or a total sum of the standardized water content index. In FIG. 12, the standardized pixel average water content index is also referred to as "pixel average" and the total sum of the standardized water content index is referred to as a "total sum". The standardized pixel average water content index and the total sum of the standardized water content index represent a water potential (in other words, application of water stress) as an index of the water content contained in the leaf (for example, leaf PT3) that is a measurement target. The standardized pixel average water content index represents a relative value at the time of setting a value (that is, an initial value) to be 1.0 when the water stress is not applied regarding the average water content in the leaf contained in each pixel constituting the visible light image area regarded as a leaf in the image obtained by imaging the leaf of the plant. Note that, as described above, the standardized pixel average water content index may be a relative value at the time of setting a value (that is, an initial value) to be 1.0 when the water stress is not applied regarding the average value obtained by dividing a total sum of the reflection intensity ratio in all the pixel areas (that is, each pixel) constituting the invisible light image of the leaf by the number of pixels. On the other hand, the total sum of the standardized water content index represents a relative value at the time of setting a value (that is, an initial value) to be 1.0 when the water stress is not applied regarding the total sum of the water content in the leaf contained in each pixel constituting the visible light image area regarded as a leaf in the image obtained by imaging the leaf of the plant. Note that, as described above, the total sum of the standardized water content index may be a relative value at the time of setting a value (that is, an initial value) to be 1.0 when the water stress is not applied regarding the total sum of the reflection intensity ratio in all the pixel areas (that is, each pixel) constituting the invisible light image of the leaf.

The horizontal axis of the graph represents the elapsed time in minutes.

The water potential control experiment as illustrated in FIG. 12 is conducted for two kinds of "Momotaro 3-1" and "Momotaro 3-2" as a kind of tomato seeding. Before the water potential control experiment as illustrated in FIG. 12, an example of the time-transition (time-serial change) of the standardized pixel average water content index and the total sum of the standardized water content index is described. For example, when the total sums of the standardized water content index of two kinds of "Momotaro 3-1" and "Momotaro 3-2" were "1.0," irrigation was not performed for five days, and after five days of non-irrigation period, water with a predetermined initial irrigation amount (for example 100 ml) was irrigated at the timing of the horizontal axis "0" so that the wilted state is recovered, and after that the irrigation (for example, 100 ml) was repeatedly performed in the morning and evening. Hereinafter, experiment results illustrated in FIG. 12 will be described. In addition, a temporal transition of the standardized pixel average water content index and the total sum of the standardized water content index as illustrated in FIG. 12 is comparatively displayed on monitor 50 (refer to FIG. 14). Note that repeated irrigation may include regular or periodic irrigation at constant time intervals every day in the morning and evening, and also may include a case where the irrigation is repeatedly performed even though the time interval is not constant every day in the morning and evening.

Specifically, as illustrated in FIG. 12, the standardized pixel average water content index of "Momotaro 3-1" and "Momotaro 3-2" starts from around a value of 0.10 indicating a state close to wilting, the standardized pixel average water content index of "Momotaro 3-1" and "Momotaro 3-2" is recovered up to be close to the value of 1.0 at the next day (that is, after one day) by the irrigation with the initial irrigation amount, and thereafter, the irrigation (for example, 100 ml) was repeatedly performed every day in the morning and evening until the lapse of ten days at the right end of the horizontal axis in FIG. 12 such that the standardized pixel average water content index is changed so as to be maintained close to the value of 1.0.

On the other hand, the following differences were found in the total sum of the standardized water content index of "Momotaro 3-1" and "Momotaro 3-2". In other words, after one day of the lapse of irrigation with the initial irrigation amount, the total sum of the standardized water content index of "Momotaro 3-1" was increased to be close the value of 1.0 after 1 day, but the total sum of the standardized water content index of "Momotaro 3-2" was increased to be only by 0.5, and after that, despite the irrigation (for example, 100 ml) was repeatedly performed every day in the morning and evening until the lapse of ten days at the right end of the horizontal axis in FIG. 12, the value was decreased from 0.5 to 0.4.

At the leftmost end of FIG. 13, a state of the leaf of "Momotaro 3-2" immediately after the irrigation with the initial irrigation amount is performed immediately after the start of the water potential control experiment illustrated in FIG. 12 is illustrated.

Two types of leaf (1) and leaf (2) are selected as comparison targets after the lapse of days.

At the center of FIG. 13, a state of the entire leaves including leaf (1) and leaf (2) of "Momotaro 3-2" after one day from the start of the water potential control experiment illustrated in FIG. 12 is illustrated. Enlarged photographs of leaf (1) and leaf (2) are illustrated. In particular, when closely viewing the enlarged photograph of the leaf (2), a slightly darker area than the surrounding green part is beginning to appear in a part of the leaf (2). That is, as illustrated in FIG. 12, there is a state where the total sum of the standardized water content index "Momotaro 3-2" has not reach the same value as the standardized pixel average water content index, but the value is halved, the partial necrosis has begun. However, even when viewing the leaf (2) at this point, it is unexpectedly difficult for the farmer to notice that the leaf (2) cells are partially necrosed in some areas of the leaf (2).

At the rightmost end of FIG. 13, a state of the entire leaves including leaf (1) and leaf (2) of "Momotaro 3-2" after the lapse of a total of six days from the start of the water potential control experiment illustrated in FIG. 12 is illustrated.

In particular, when viewing the enlarged photograph of the leaf (2), in a considerable area of the leaf (2) (for example, an area about 50% of the whole of the leaf (2)), an area which seems to be ocher compared to the surrounding green part has appeared.

This illustrates that excessive stress (for example, water stress) is applied when necessary water was not supplied to the leaf (2) for five days before the control experiment and further six days with non-irrigation from the control experiment, and thus the cells of the leaf (2) are partially necrotic. At this point, when the farmer views the leaf (2), it is possible to visually confirm the existence of the partial necrosis. As such, the decrease in the total sum of the standardized water content index is interpreted as partial necrosis (in other words, partial cell destruction that makes photosynthesis no longer capable of being performed), and as a result, due to the difference in the total sum of the standardized water content index illustrated in FIG. 12, photosynthetic ability of "Momotaro 3-2" becomes nearly half of the photosynthetic ability of "Momotaro 3-1".

When there is partial necrosis in the leaf or there the sign thereof, the value of the water content index in the pixel corresponding to the corresponding area becomes lower, which is smaller than threshold level Sh for being regarded as a leaf. For this reason, the total sum of the standardized water content index of the leaf (for example, refer to "Momotaro 3-2" illustrated in FIG. 12) becomes smaller as a whole than the total sum of the standardized water content index of the leaf at which partial necrosis does not occur at all (for example, refer to "Momotaro 3-1" illustrated in FIG. 12). On the other hand, even if there is partial necrosis in the leaf or there is a sign thereof, the standardized pixel average water content index of such a leaf corresponds to a value obtained by dividing a total sum of the reflection intensity ratio in each pixel corresponding to the visible light image area regarded as a leaf or each pixel constituting the invisible light image of the leaf by the number of pixels, and thus even if there is partial necrosis, the fact that such phenomenon has occurred does not appear clearly as a numerical value. In other words, there is no apparent difference between the standardized pixel average water content index of the leaf where partial necrosis does not occur and the standardized pixel average water content index of the leaf with the partial necrosis or the sign thereof.

Therefore, in the present embodiment, attention is paid to the fact that there is a difference in the total sum of the standardized water content index of the leaf having partial necrosis or the sign thereof and the leaf without the partial necrosis or the sign thereof, and in one or two or more kinds of leaves as illustrated in FIG. 12, the time-transition of each of the standardized pixel average water content index and the total sum of the standardized water content index which are calculated by plant detection camera 1 are displayed on monitor 50. As a result, the farmer does not need to frequent visit to a growing place such as a greenhouse, a field, and the like, or a farm, and by confirming the time-transition of the standardized pixel average water content index and the total sum of the standardized water content index comparatively displayed on monitor 50, for example, it is possible to easily grasp the presence or absence of the partial necrosis of "Momotaro 3-2" or the presence or absence of the sign of the necrosis with high accuracy. In addition, the farmer can detect the sign of the partial necrosis, and thus can take measure against the application of optimum water stress (prediction of the irrigation timing, for example).

Figure 14:
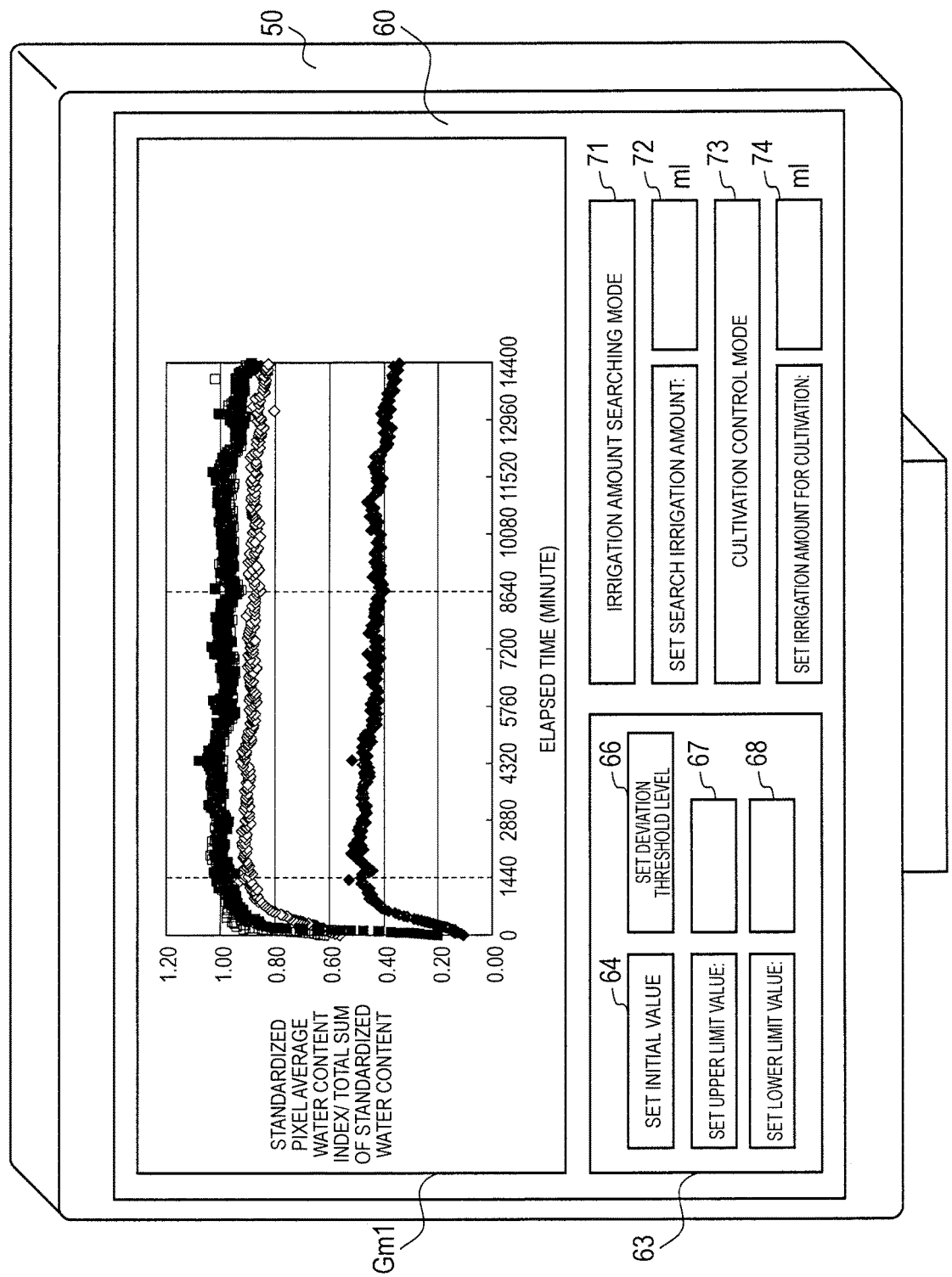
FIG. 14 is a diagram illustrating an example of a user interface (UI) screen relating to the water potential control experiment.

FIG. 14 is a diagram illustrating an example of user interface (UI) screen 60 relating to the water potential control experiment. UI screen 60 includes screen for monitoring water content in leaf Gm1. A graph comparatively representing a time-transition of each of the standardized pixel average water content index and the total sum of the standardized water content index is displayed on screen for monitoring water content in leaf Gm1 disposed on the upper portion of UI screen 60. This graph is similar to the graph of FIG. 12 described above.

Set area 63 is displayed on the left side of the lower portion of UI screen 60. Initial value setting button 64 and deviation threshold level setting button 66 are disposed in set area 63. Also, input box 67 for setting the upper limit value of the range of a target standardized pixel average water content index (that is, a target range) in order to appropriately apply the water stress, and input box 68 for inputting the lower limit value of the range of a similar target standardized pixel average water content index (that is, a target range) are disposed.

For inputting numerical values to input boxes 67 and 68, it is possible to use a touch panel, a numeric keypad, a portable terminal, or the like.

In addition, irrigation amount searching mode button 71 and water stress control (cultivation control) mode button 73 are disposed on the right side of the lower portion of UI screen 60. When irrigation amount searching mode button 71 is pressed, the optimum irrigation water amount searching operation for searching for an appropriate value as an irrigation amount of the water to be irrigated at once is started. When water stress control (cultivation control) mode button 73 is pressed, the cultivation control operation for which an appropriate irrigation amount is searched, and irrigation is actually performed with the appropriate irrigation amount is started. Further, on UI screen 60, display box 72 for displaying a setting value of the search irrigation amount and display box 74 for displaying a setting value of the irrigation amount for cultivation are disposed.

Figure 15:
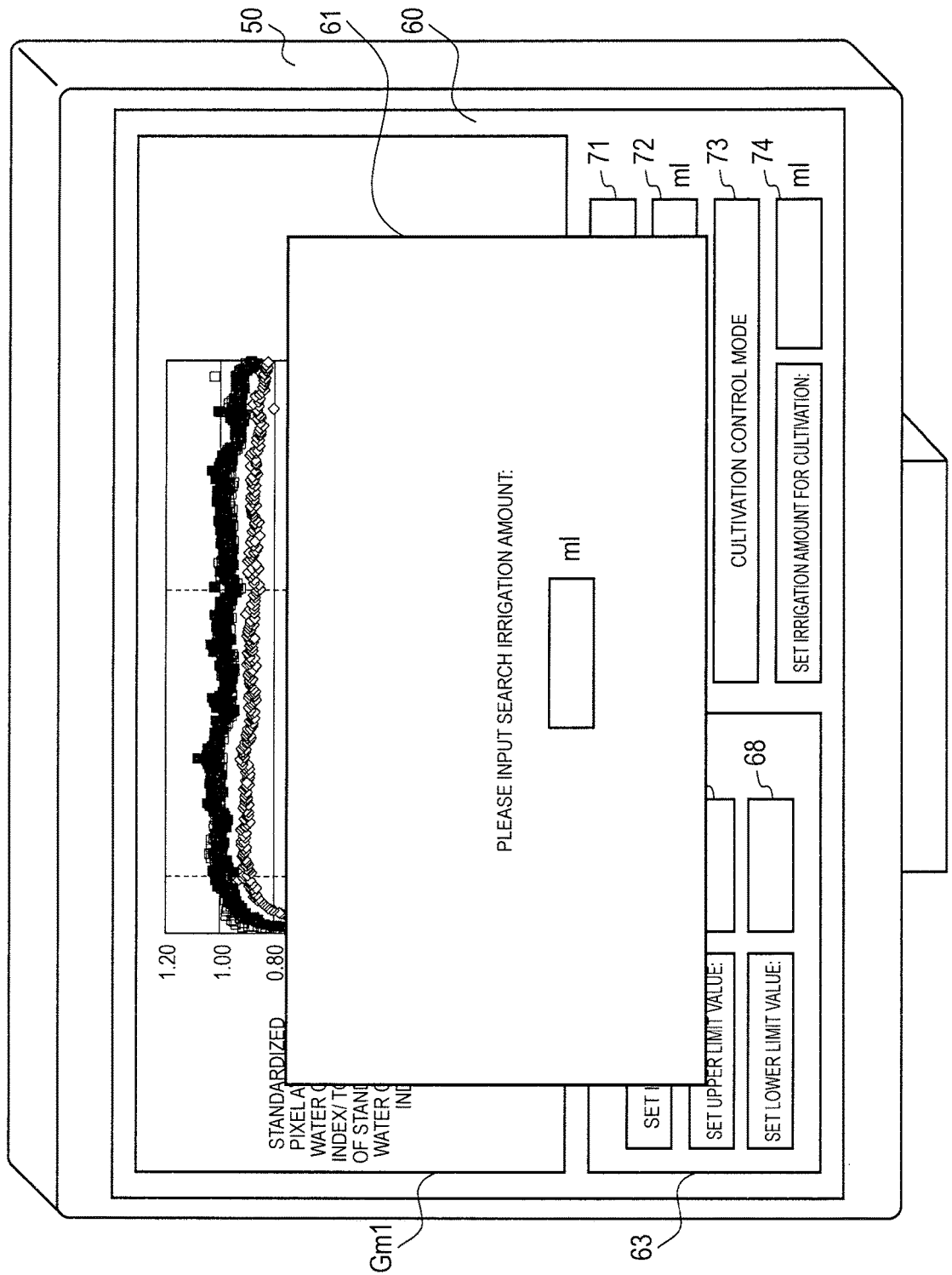
FIG. 15 is a diagram illustrating an example of an initial irrigation amount input screen pop-up displayed on a UI screen.

FIG. 15 is a diagram illustrating an example of initial irrigation amount input screen 61 pop-up displayed on UI screen 60. In initial irrigation amount input screen 61, for example, the initial irrigation amount is input and set by unit of milliliter (ml). A touch panel, a numeric keypad, a mobile terminal, and the like can be used for inputting the initial irrigation amount.

Figure 16:
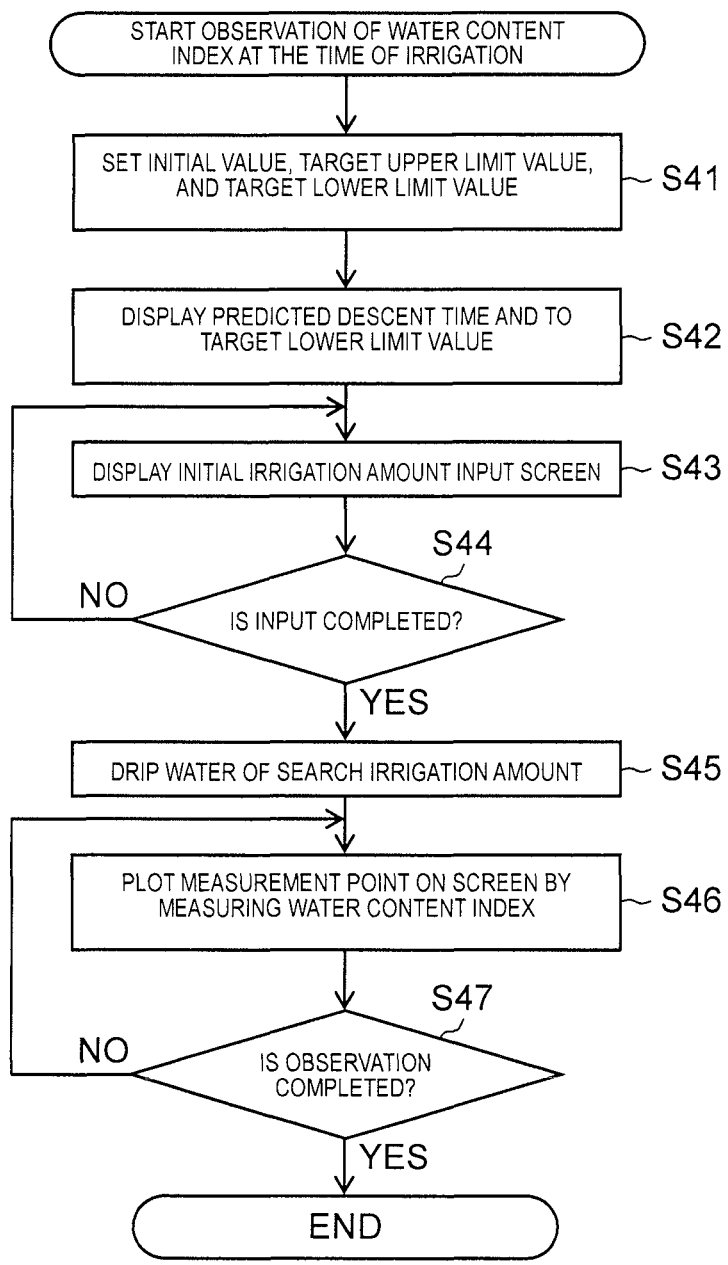
FIG. 16 is a flow chart illustrating an observing operation procedure of the water content index at the time of irrigation in the present embodiment.

FIG. 16 is a flow chart illustrating an observing operation procedure of the water content index at the time of irrigation in the present embodiment. The operation of observing the water content index of FIG. 16 is executed, for example, when cultivation control mode button 73 is pressed on UI screen 60 illustrated in FIG. 14.

In an observing operation of the water content index, first, controller 11 sets an initial value, and the upper limit value and the lower limit value of target range by the operation of a user (for example, a farmer who is a user of tomatoes) with respect to UI screen 60 (S41). Controller 11 displays the predicted descent time to the lower limit value of the target range in a case where time has elapsed with in a state where the current environmental conditions (for example, temperature and humidity) in the greenhouse are maintained (S42).

Controller 11 displays initial irrigation amount input screen 61 illustrated in FIG. 15 (S43). Controller 11 determines whether or not the input of the initial irrigation amount has been completed (S44), and if the input is not completed, controller 11 continues to display initial irrigation amount input screen 61 in step S43.

In addition, when the input of the initial irrigation amount is completed, controller 11 controls dripping of water corresponding to the initial irrigation amount input on initial irrigation amount input screen 61 (S45). In addition, the dripping of the water of the initial irrigation amount may be automatically performed by fertilizer or water supply device WF, or may be performed manually by a person (for example, a farmer). Thereafter, controller 11 calculates and measures each of the standardized pixel average water content index and the total sum of the standardized water content index of the leaf that is a target of the observation operation, and plots and adds the measurement point to the corresponding portion of the graph in screen for monitoring water content in leaf Gm1 displayed on UI screen 60 (S46). Controller 11 determines whether or not to end the observation operation (S47), and in a case where it is determined to end the observation operation (YES in S47), controller 11 ends the process illustrated in FIG. 16.

On the other hand, controller 11 repeats the process of step S46 until it determines to end the observation operation. The case where it is determined to end the observation operation includes, for example, a case where time has reached the time set in advanced and a case where an operation for instructing the end of the observation operation is input to controller 11 by a user such as a farmer.

Figure 17:
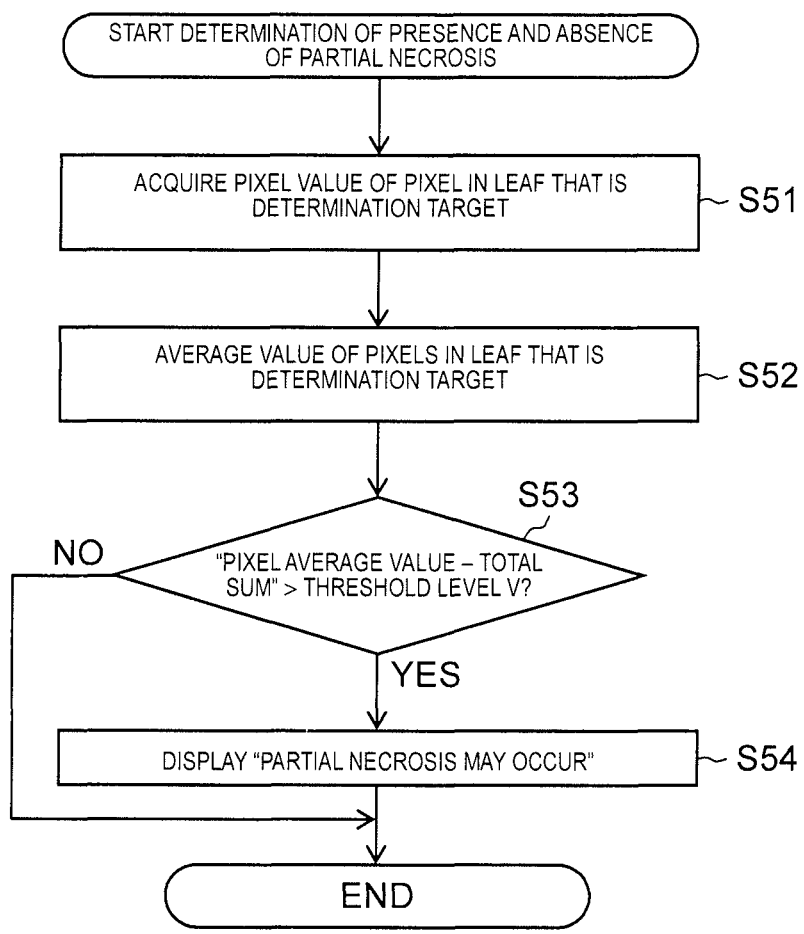
FIG. 17 is a flow chart illustrating an example of a determining operation presence and absence of partial necrosis or its sign in the present embodiment.

FIG. 17 is a flow chart illustrating an example of a determining operation presence and absence of partial necrosis or its sign in the present embodiment;

The determining operation of FIG. 17 is executed in parallel and independently of the process of step S46 shown in FIG. 16, for example.

In the operation of determining whether or not there is the partial necrosis or the sign thereof, controller 11 first acquires the pixel value (that is, the reflection intensity ratio for each pixel, for example, refer to step S31 in FIG. 8) of the pixel (that is each pixel for constituting a captured image of the leaf to be determined (S51).

Using the output (that is, the pixel value) of step S51, controller 11 calculates the average value of the pixel values of the pixels in the leaf to be determined (in other words, the area of the visible light image regarded as a leaf or the standardized pixel average water content index in the area of the invisible light image of the leaf) and the total sum in the leaf (in other words, the total sum of the standardized water content index in the area of the visible light image regarded as a leaf or the area of the invisible light image of the leaf) (S52).

Controller 11 determines whether or not the difference between the standardized pixel average water content index and the total sum of the standardized water content index is larger than a predetermined threshold level V by using the output of step S52 (that is, the standardized pixel average water content index and the total sum of the standardized water content index) (S53).

In the case where the difference between the standardized pixel average water content index and the total sum of the standardized water content index is not larger than a predetermined threshold level V (NO in S53), the standardized pixel average water content index and the total sum of the standardized water content index are approximately the same as each other, and when it is determined that there is no sign of partial necrosis in the leaf, the processing of controller 11 is completed.

On the other hand, in the case where it is determined that the difference between the standardized pixel average water content index and the total sum of the standardized water content index is larger than a predetermined threshold level V (YES in S53), controller 11 displays a message that "partial necrosis may occur" on monitor 50 with respect to the leaf to be determined (S54).

As described above, in plant detection camera 1 according to the present embodiment, first beam source 13 of plant detection camera 1 performs optical scanning so that the near infrared light (reference light) of the first wavelength (905 nm), which has a characteristic in which light tends not to be absorbed in water is radiated toward leaf PT3 that is a target portion of plant PT. Second beam source 15 of plant detection camera 1 performs optical scanning so that the near infrared light (reference light) of the second wavelength (1550 nm), which has a characteristic easily absorbed by water is radiated toward leaf PT3 of plant PT. Display processor 29 as an example of an output unit outputs an invisible light image of a target portion to be observed of the plant (that is, one of a leaves, fruits, stems, roots and flowers, for example leaves). Based on the reflection light of 905 nm reflected at all the irradiation positions of leaf PT3 and the reflection light of 1550 nm reflected at all irradiation positions of leaf PT3, threshold level setter/water content index detector 27a calculates, for example, the reflection intensity ratio as the water content contained in the pixel for each pixel area (that is, one pixel) constituting the invisible light image of leaf PT that is a target portion, and calculate the total sum ($I_{905}/I_{1550}$) of the reflection intensity ratios as a total sum of the water content index.

Controller 11 displays, as the time-transition of the water content in the target portion (for example, leaf PT3) from the start of the measurement period, the total sum of the standardized water content index and the standardized pixel average water content index in the target portion (for example, leaf PT3) based on the standardized pixel average water content index and the total sum of the standardized water content index for each calculated pixel area on UI screen 60 of monitor 50 in a comparative manner.

As described above, according to plant detection camera 1, when a graph illustrating the total sum of the standardized water content index in all the pixels for constituting the invisible light image of leaf PT3 and the standardized pixel average water content index in all the pixel areas constituting the invisible light image of leaf PT3 is displayed on UI screen 60 of monitor 50 as the time-transition of the water content contained in leaf PT3 of plant PT, it is possible to contribute to the early teaching whether or not the state of applying the water stress to the plant and the state of partial necrosis has occurred. In addition, according to the time-transition of the standardized pixel average water content index and the total sum of the standardized water content index contained in leaf PT3 displayed on UI 60 of monitor 50, plant detection camera 1 can teach the user that the leaves in which the total sum of the standardized water content index is relatively smaller than the standardized pixel average water content index may be treated as unnecessary. As a result, the user can remove the leaves as a target of the leafing operation. In other words, since the extra leaves are removed, sufficient nutrients are supplied to other healthy leaves (that is, young leaves) which are to be provided with nutrients originally, so that it is possible to contribute the growth of young leaves. Furthermore, since a message indicating that there is a sign of the partial necrosis is displayed on monitor 50, it is possible to indicate the value of the total sum of the standardized water content index to the user as a reference value when determining that the total sum of the standardized water content index targeted as a subject of aging.

Note that, when viewed from first beam source 13 and second beam source 15, white reference substrate bd (background material) which covers a back surface of leaf PT3 of plant PT is disposed on leaf PT3 of plant PT. With this, with plant detection camera 1, it is possible to eliminate influence due to scattered light (light scattered externally) from the peripheral leaf and accurately measure the water content of leaf PT3 even within the foliage in which multiple leaves grow in abundance on a periphery of leaf PT3 that is the measurement target portion of plant observation.

Further, according to plant detection camera 1, as the time-transition of the water content contained in the target portion (the is leaf) of the plant, the change in the water content based on non-irrigation of, for example, five days before the start of the measurement period and irrigation with the initial irrigation amount (for example 100 ml) at start of the measurement period, and repeated irrigation toward the plant after the irrigation with the initial irrigation amount is displayed. As a result, the user can quantitatively grasp the chronological influence of the irrigation with the initial irrigation amount on the plant in a state where the water stress is intentionally applied by non-irrigation.

Further, a plurality of plants that are observation targets of plant detection camera 1 may be provided, and plant detection camera 1 may display, as the time-transition of the water content contained in the target portion (for example, leaf) for each plant, and displays the standardized pixel average water content index and the total sum of the standardized water content index on monitor 50 in a comparative manner. As a result, the user can easily determine the presence or absence of partial necrosis or the sign thereof from the time-transition of the water content contained in the leaf as the target portion while comparing the respective plants.

According to the plant detection camera 1, it is also determined whether or not the difference between the standardized pixel average water content index and the total sum of the standardized water content index in the target portion (for example. leaf leaves) of the plant is larger than a predetermined threshold level V. With this, plant detection camera 1 can easily determine the presence or absence of the partial necrosis or the sign of the partial necrosis in the target portion (for example, leaf) of the plant.

Further, according to plant detection camera 1, in the case where it is determined that the difference between the standardized pixel average water content index and the total sum of the standardized water content index in the target portion (for example, a leaf) of the plant is larger than a predetermined threshold level V, plant detection camera 1 displays a message that points out possibility of necrosis on monitor 50

As a result, the use does not need to frequent visit to a growing place such as a greenhouse, a field, and the like, or a farm, and by confirming the time-transition of the standardized pixel average water content index and the total sum of the standardized water content index comparatively displayed on monitor 50, for example, it is possible to easily grasp the presence or absence of the partial necrosis of "Momotaro 3-2" or the presence or absence of the precursor of the necrosis with high accuracy.

Although various embodiments are described above while referring to the drawings, needless to say, the present disclosure is not limited to Examples. It is obvious that it is possible for those skilled in the art to conceive of various Modification Examples and Correction Examples within the scope which is set forth in the claims, and therein is naturally understood as belonging to the technical scope of the present disclosure.

Meanwhile, in the description of the cultivation device of the present embodiment described above, the process of non-irrigation such as interrupting irrigation to the plant was performed in order to apply stress (for example, water stress) to the plant (for example, leaf of tomato). However, in the cultivation device of the present embodiment, the method of applying the stress (for example, water stress) to the plant is not limited to the non-irrigation. For example, in order to apply the stress (for example, water stress) to the plant, for example, the cultivation device of the present embodiment may change the electric conductivity of the liquid fertilizer (that is, liquid fertilizer) which is supplied to the plant to be equal to or larger than a predetermined value without using the non-irrigation. In other words, the cultivation device consequently applies water stress equivalent to the non-irrigation to the plant by changing the electric conductivity of the liquid fertilizer so that the electric conductivity of the liquid fertilizer is equal to or larger than a predetermined value. The reason for this is that when the electric conductivity of the liquid fertilizer is changed so as to be equal to or larger than a predetermined value, the root cannot absorb water due to an osmotic pressure relationship (in other words, salt stress is applied), and as a result, the water stress is applied to the plant similar to the case of non-irrigation. Note that, the aforementioned predetermined value is a known value obtained from the experience of the user and is the lower limit value of the electric conductivity of the liquid fertilizer when the salt stress is applied to the plant.

INDUSTRIAL APPLICABILITY

The present disclosure provides quantitatively and time-serially transition of a water content contained in a plant and is useful as a device for observing water content, a method for observing water content, and a cultivation device which are capable of contributing to the early teaching whether or not the state of applying the water stress to the plant and the state of partial necrosis has occurred.

REFERENCE MARKS IN THE DRAWINGS

1 PLANT DETECTION CAMERA
11 CONTROLLER
11a TIMING CONTROLLER
13 FIRST BEAM SOURCE
15 SECOND BEAM SOURCE
17 BEAM SCANNER
21, 31 IMAGING OPTICS
23, 33 PHOTO DETECTOR
25 SIGNAL PROCESSOR
25a I/V CONVERTER
25b AMPLIFIER
25c COMPARATOR/PEAK HOLD
27 DETECTION PROCESSOR
27a THRESHOLD LEVEL SETTER/WATER CONTENT INDEX DETECTOR
27b MEMORY
27c DETECTION RESULT FILTER
29 DISPLAY PROCESSOR
35 IMAGE SIGNAL PROCESSOR
37 DISPLAY CONTROLLER
50 MONITOR
60 UI (USER INTERFACE) SCREEN
61 INITIAL IRRIGATION AMOUNT INPUT SCREEN
63 SET AREA
64 INITIAL VALUE SETTING BUTTON
66 DEVIATION THRESHOLD LEVEL SETTING BUTTON
67, 68 INPUT BOX
71 IRRIGATION AMOUNT SEARCHING MODE BUTTON 71
72, 74 DISPLAY BOX
73 WATER STRESS CONTROL (CULTIVATION CONTROL) MODE BUTTON
bd WHITE REFERENCE SUBSTRATE
bd1 APERTURE
bd2 HOLE
bd3, bd4, bd5, bd21 SLIT
Gm1 SCREEN FOR MONITORING WATER CONTENT IN LEAF
JG DETERMINER
PT3, PT3t, PT3o LEAF
LS1 REFERENCE BEAM
LS2 MEASURING BEAM
MT COMMUNICATION TERMINAL
NVSS INVISIBLE LIGHT SENSOR
PJ BEAM OUTPUT
TR TIMING SIGNAL FOR BEAM SCANNING
RF BEAM OUTPUT SIGNAL
RV0 AMBIENT LIGHT
RV1, RV2 DIFFUSE REFLECTION LIGHT
VSC VISIBLE LIGHT CAMERA
W1, Wk REFLECTION INTENSITY RATIO
WF FERTILIZER WATER SUPPLY DEVICE

The invention claimed is:

1. A device for observing water content contained in a plant, the device comprising:
    a first light source which radiates a near infrared laser reference beam of a first wavelength having a characteristic in which light tends not to be absorbed in water while sequentially scanning toward the plant;
    a second light source which radiates a near infrared laser measuring beam of a second wavelength having a characteristic in which light tends to be absorbed in water while sequentially scanning toward the plant;
    an output unit that outputs an invisible light image of a target portion to be observed of the plant;
    a water content calculation unit that repeatedly calculates the water content contained in each pixel area constituting the invisible light image based on reflection light of the near infrared laser reference beam and reflection light of the near infrared laser measuring beam, in a certain measurement period; and
    a controller that displays, as a time-transition of the water content in the target portion from start of the measurement period, a pixel average value of the water content in the target portion and a total sum of the water content in the target portion using the water content contained in the pixel area calculated by the water content calculation unit on a display unit in a comparative manner.

2. The device for observing water content of claim 1, wherein a background material which covers a back surface of the plant is disposed in the plant as seen from the first light source and second light source.

3. The device for observing water content of claim 1, wherein the controller displays, as a time-transition of water content of the target portion, a change of the water content based on irrigation with an initial irrigation amount at start of the measurement period and non-irrigation to the plant after the irrigation with the initial irrigation amount.

4. The device for observing water content of claim 1, wherein a plurality of the plants are provided, and wherein the controller displays the time-transition of the water content of the target portion calculated by the water content calculation unit, in each plant.

5. The device for observing water content of claim 1, wherein the controller determines whether or not a difference between the pixel average value of the water content in the target portion and the total sum of the water content in the pixel area is larger than a threshold.

6. The device for observing water content of claim 5, wherein the controller displays a message that points out possibility of partial necrosis of the target portion of the plant on the display unit in a case where it is determined that the difference between the pixel average value of the water content in the target portion and the total sum of the water content in all the pixel area is equal to or larger than the threshold.

7. A cultivation device comprising:
the device for observing water content of claim 1; and
a cultivation controller that performs irrigation with a set initial irrigation amount on the plant at start of a measurement period.

8. A method for observing water content in a device for observing water content contained in a plant, the method comprising:
radiating a near infrared laser reference beam of a first wavelength having a characteristic in which light tends not to be absorbed in water while sequentially scanning toward the plant, by a first light source;
radiating a near infrared laser measuring beam of a second wavelength having a characteristic in which light tends to be absorbed in water while sequentially scanning toward the plant, by a second light source;
outputting an invisible light image of a target portion to be observed of the plant;
repeatedly calculating the water content contained in each pixel area constituting the invisible light image based on reflection light of the near infrared laser reference beam and reflection light of the near infrared laser measuring beam, in a certain measurement period; and
displaying, as a time-transition of the water content in the target portion from start of the measurement period, a pixel average value of the water content in the target portion and a total sum of the water content in the target portion using the calculated water content contained in the pixel area on a display unit in a comparative manner.

* * * * *